United States Patent
Ichihashi et al.

(10) Patent No.: US 7,645,278 B2
(45) Date of Patent: Jan. 12, 2010

(54) COAGULATING CUTTER

(75) Inventors: Hiroshi Ichihashi, Sagamihara (JP); Ryoji Sakai, Hachioji (JP); Masaru Imoto, Machida (JP); Masami Oshida, Kanagawa (JP); Katsumi Sasaki, Tokyo (JP)

(73) Assignee: Olympus Corporation (JP)

( * ) Notice: Subject to any disclaimer, the term of this patent is extended or adjusted under 35 U.S.C. 154(b) by 544 days.

(21) Appl. No.: 11/359,535

(22) Filed: Feb. 22, 2006

(65) Prior Publication Data
US 2007/0198005 A1 Aug. 23, 2007

(51) Int. Cl.
*A61B 18/18* (2006.01)

(52) U.S. Cl. .............................. 606/51; 606/52; 606/40; 606/50

(58) Field of Classification Search ................... 606/27, 606/32, 37, 39, 40, 46, 41, 49, 51, 52
See application file for complete search history.

(56) References Cited

U.S. PATENT DOCUMENTS

| | | | | |
|---|---|---|---|---|
| 3,643,663 A | * | 2/1972 | Sutter | 606/51 |
| 3,834,392 A | * | 9/1974 | Lampman et al. | 606/52 |
| 3,920,021 A | * | 11/1975 | Hiltebrandt | 606/50 |
| 3,945,375 A | * | 3/1976 | Banko | 600/104 |
| 4,041,952 A | * | 8/1977 | Morrison et al. | 606/42 |
| 4,375,218 A | * | 3/1983 | DiGeronimo | 606/52 |
| 4,492,231 A | * | 1/1985 | Auth | 606/42 |

(Continued)

FOREIGN PATENT DOCUMENTS

JP 8-505801 6/1996

(Continued)

OTHER PUBLICATIONS

International Search Report issued Mar. 27, 2007 in connection with corresponding application No. PCT/JP2007/053087.

(Continued)

*Primary Examiner*—Linda C Dvorak
*Assistant Examiner*—Amanda Scott
(74) *Attorney, Agent, or Firm*—Ostrolenk Faber LLP

(57) ABSTRACT

A coagulating cutter according to the present invention comprises: a transmitting member for transmitting energy, for treating living body tissue, to the living body tissue; an outer sheath through which the transmitting member is passed; and a grasping section supported at the tip end portion of the outer sheath so as to be capable of turning with respect to the transmitting member, which allows the living body tissue to be grasped against the transmitting member. With such an arrangement, upon turning the grasping section toward the transmitting member to be in a closed state, the faces of the transmitting member and the grasping section, which face each other, provide a contact portion, where the transmitting member and the grasping section are in contact with each other over a predetermined length, for incising the living body tissue grasped between the transmitting member and the grasping section, and a non-contact portion, where the transmitting member and the grasping section are provided with a predetermined interval on both sides of the axis extending in the direction of the predetermined length of the contact portion so as not to be in contact with each other, for coagulating the living body tissue.

3 Claims, 16 Drawing Sheets

U.S. PATENT DOCUMENTS

| | | | | |
|---|---|---|---|---|
| 4,597,379 A | * | 7/1986 | Kihn et al. | 606/40 |
| 4,644,950 A | * | 2/1987 | Valli | 606/46 |
| 4,657,018 A | * | 4/1987 | Hakky | 606/46 |
| 4,660,571 A | * | 4/1987 | Hess et al. | 607/116 |
| 4,671,274 A | * | 6/1987 | Sorochenko | 606/51 |
| 4,732,149 A | * | 3/1988 | Sutter | 606/51 |
| 4,920,982 A | * | 5/1990 | Goldstein | 128/842 |
| 5,026,370 A | * | 6/1991 | Lottick | 606/42 |
| 5,049,148 A | * | 9/1991 | Mehl | 606/43 |
| 5,116,332 A | * | 5/1992 | Lottick | 606/42 |
| 5,122,139 A | * | 6/1992 | Sutter | 606/51 |
| 5,147,356 A | * | 9/1992 | Bhatta | 606/37 |
| 5,147,357 A | * | 9/1992 | Rose et al. | 606/49 |
| 5,207,691 A | * | 5/1993 | Nardella | 606/142 |
| 5,258,006 A | * | 11/1993 | Rydell et al. | 606/205 |
| 5,295,990 A | * | 3/1994 | Levin | 606/49 |
| 5,304,183 A | * | 4/1994 | Gourlay et al. | 606/142 |
| 5,306,287 A | * | 4/1994 | Becker | 606/205 |
| 5,322,055 A | * | 6/1994 | Davison et al. | 601/2 |
| 5,342,359 A | * | 8/1994 | Rydell | 606/51 |
| 5,342,381 A | * | 8/1994 | Tidemand | 606/174 |
| 5,352,222 A | * | 10/1994 | Rydell | 606/37 |
| 5,354,296 A | * | 10/1994 | Turkel | 606/41 |
| 5,360,428 A | * | 11/1994 | Hutchinson, Jr. | 606/45 |
| 5,380,320 A | * | 1/1995 | Morris | 606/33 |
| 5,396,900 A | * | 3/1995 | Slater et al. | 600/564 |
| 5,403,312 A | * | 4/1995 | Yates et al. | 606/50 |
| 5,443,463 A | * | 8/1995 | Stern et al. | 606/51 |
| 5,445,638 A | * | 8/1995 | Rydell et al. | 606/51 |
| 5,458,598 A | * | 10/1995 | Feinberg et al. | 606/52 |
| 5,462,546 A | * | 10/1995 | Rydell | 606/51 |
| 5,540,684 A | * | 7/1996 | Hassler, Jr. | 606/40 |
| 5,569,243 A | * | 10/1996 | Kortenbach et al. | 606/46 |
| 5,688,270 A | * | 11/1997 | Yates et al. | 606/51 |
| 5,693,051 A | * | 12/1997 | Schulze et al. | 606/51 |
| 5,700,261 A | * | 12/1997 | Brinkerhoff | 606/41 |
| 5,702,390 A | * | 12/1997 | Austin et al. | 606/48 |
| 5,707,369 A | * | 1/1998 | Vaitekunas et al. | 606/31 |
| 5,741,285 A | * | 4/1998 | McBrayer et al. | 606/170 |
| 5,776,130 A | * | 7/1998 | Buysse et al. | 606/48 |
| 5,807,393 A | * | 9/1998 | Williamson et al. | 606/32 |
| 5,810,811 A | * | 9/1998 | Yates et al. | 606/50 |
| 5,827,279 A | * | 10/1998 | Hughett et al. | 606/45 |
| 5,893,846 A | * | 4/1999 | Bales et al. | 606/32 |
| 5,908,420 A | * | 6/1999 | Parins et al. | 606/51 |
| 5,925,041 A | * | 7/1999 | Long et al. | 606/41 |
| 5,944,718 A | * | 8/1999 | Austin et al. | 606/48 |
| 5,954,720 A | * | 9/1999 | Wilson et al. | 606/50 |
| 5,961,514 A | * | 10/1999 | Long et al. | 606/41 |
| 6,003,517 A | * | 12/1999 | Sheffield et al. | 128/898 |
| 6,010,516 A | * | 1/2000 | Hulka | 606/148 |
| 6,024,741 A | * | 2/2000 | Williamson et al. | 606/40 |
| 6,039,733 A | * | 3/2000 | Buysse et al. | 606/40 |
| 6,086,586 A | * | 7/2000 | Hooven | 606/50 |
| 6,117,132 A | * | 9/2000 | Long et al. | 606/41 |
| H001904 H | * | 10/2000 | Yates et al. | 606/50 |
| 6,152,923 A | * | 11/2000 | Ryan | 606/51 |
| 6,179,834 B1 | * | 1/2001 | Buysse et al. | 606/41 |
| 6,179,836 B1 | * | 1/2001 | Eggers et al. | 606/45 |
| 6,179,837 B1 | * | 1/2001 | Hooven | 606/50 |
| 6,187,002 B1 | * | 2/2001 | Long et al. | 606/46 |
| 6,190,386 B1 | * | 2/2001 | Rydell | 606/51 |
| 6,193,709 B1 | * | 2/2001 | Miyawaki et al. | 606/1 |
| 6,558,376 B2 | * | 5/2003 | Bishop | 606/27 |
| 6,613,048 B2 | * | 9/2003 | Mulier et al. | 606/49 |
| 6,702,813 B1 | * | 3/2004 | Baxter et al. | 606/49 |
| 6,743,229 B2 | * | 6/2004 | Buysse et al. | 606/51 |
| 6,755,827 B2 | * | 6/2004 | Mulier et al. | 606/49 |
| 6,770,072 B1 | * | 8/2004 | Truckai et al. | 606/52 |
| 6,773,409 B2 | * | 8/2004 | Truckai et al. | 601/2 |
| 6,776,780 B2 | * | 8/2004 | Mulier et al. | 606/51 |
| 6,887,252 B1 | | 5/2005 | Okada et al. | |
| 7,131,970 B2 | * | 11/2006 | Moses et al. | 606/51 |
| 7,361,172 B2 | * | 4/2008 | Cimino | 606/27 |
| 7,384,420 B2 | * | 6/2008 | Dycus et al. | 606/51 |
| 7,396,356 B2 | * | 7/2008 | Mollenauer | 606/51 |
| 7,422,590 B2 | * | 9/2008 | Kupferschmid et al. | 606/51 |
| 7,422,591 B2 | * | 9/2008 | Phan | 606/51 |
| 2001/0037109 A1 | | 11/2001 | Yamauchi et al. | |
| 2003/0114874 A1 | * | 6/2003 | Craig et al. | 606/169 |

FOREIGN PATENT DOCUMENTS

| | | |
|---|---|---|
| JP | 08-275951 | 10/1996 |
| JP | 2000-254138 | 9/2000 |
| JP | 2002-224133 | 8/2002 |
| JP | 2005-51219 | 5/2005 |
| WO | WO 9308754 A1 * | 5/1993 |
| WO | WO 03/082133 | 10/2003 |

OTHER PUBLICATIONS

European Search Report and Search Opinion dated Mar. 10, 2009 in corresponding European Application No. EP 07 71 4590.

* cited by examiner

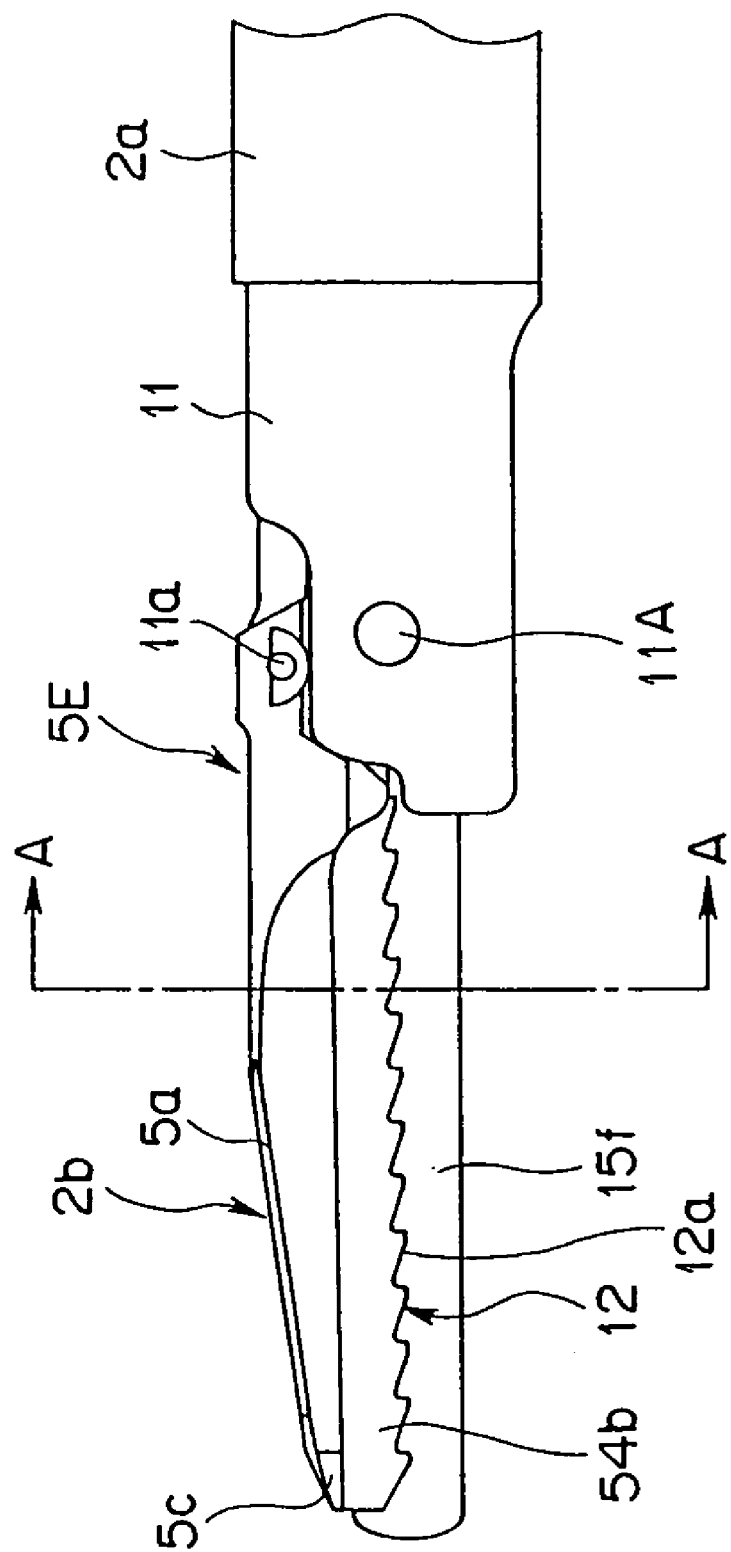

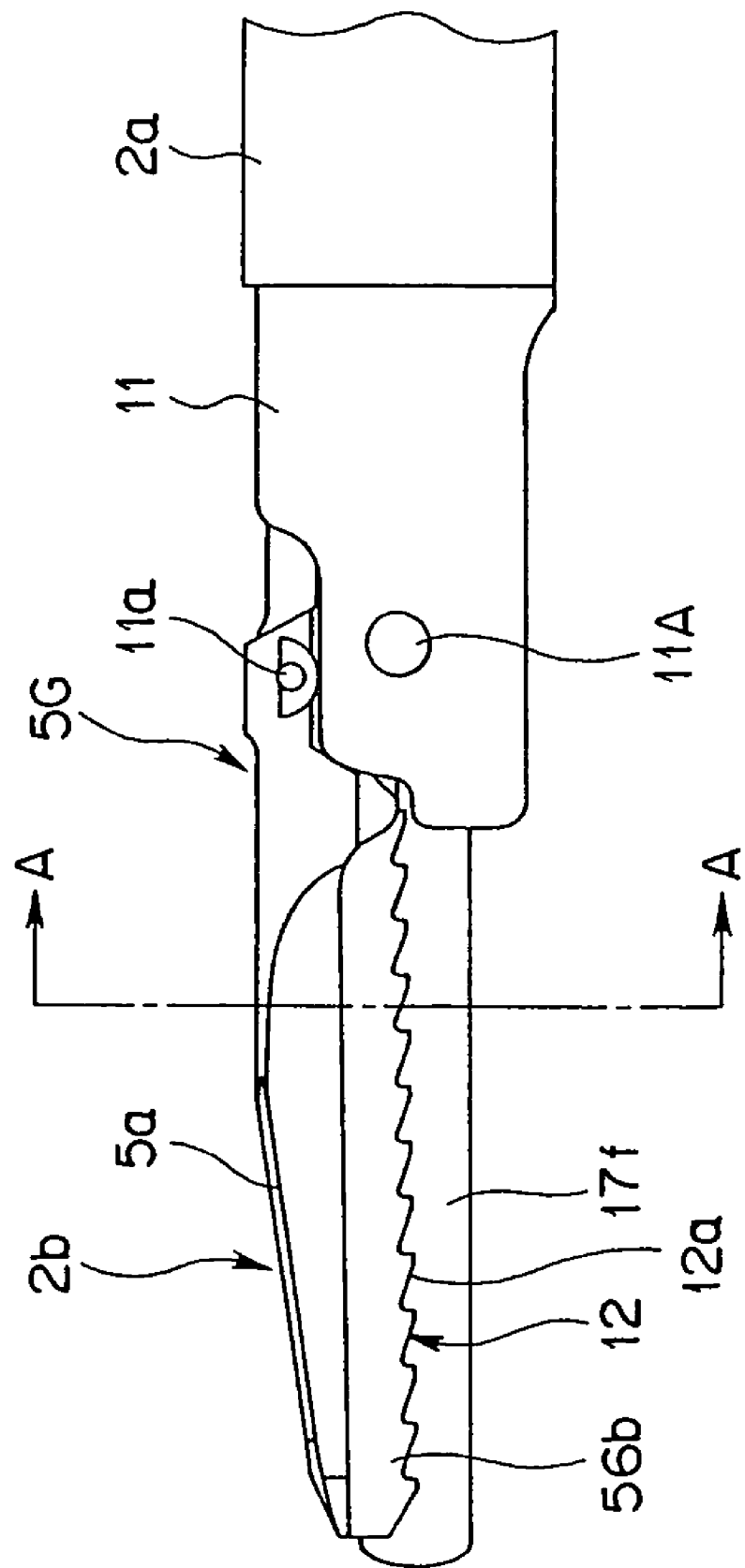

COAGULATING CUTTER

BACKGROUND OF THE INVENTION

1. Field of the Invention

The present invention relates to a coagulating cutter, and more particularly relates to a coagulating cutter wherein living body tissue is grasped between an ultrasonic probe and a jaw, and the living body tissue is subjected to treatment such as incision, excision, coagulation, or the like.

2. Description of the Related Art

As of recent years, procedures have come to be performed wherein a slender endoscope is inserted into the body cavity so as to observe organs within the body cavity, and perform various types of medical treatment under endoscopic observation as necessary.

One known method of the aforementioned medical treatment performed under endoscopic observation is to perform medical treatment using a coagulating cutter. In the event that such a coagulating cutter uses ultrasonic waves for example as the energy for subjecting the living body to treatment, the coagulating cutter has a function which enables treatment for the living body tissue such as incision, excision, coagulation, or the like, to be performed with the living body tissue being grasped between an ultrasonic probe and a jaw.

Generally, such a coagulating cutter has a configuration in which an operator-side operating unit is connected to the base end portion of an outer sheath of an insertion portion, with an ultrasonic transducer for generating ultrasonic vibrations being disposed at this operating unit and a treating section for treating the living body tissue being disposed on the tip portion of the outer sheath of the insertion portion.

Also, a vibration transmitting member is inserted through the interior of the outer sheath of the insertion portion, which provides a function of transmitting ultrasonic vibration from the ultrasonic transducer to an ultrasonic probe situated on the treating-section side. The base end portion of the vibration transmitting member is connected to the ultrasonic transducer. Furthermore, a jaw is disposed on the treating section so as to be capable of turning relative to the ultrasonic probe.

Also, an operating handle for performing opening/closing operations of the jaw relative to the ultrasonic probe is provided to the operating unit. Furthermore, a jaw operating rod is inserted through the interior of the outer sheath of the insertion portion so as to be capable of advancing/retracting in the axial direction. The operating rod advances/retracts in the axial direction in accordance with the operations of the operating handle. Furthermore, the jaw of the treating section performs opening/closing operations relative to the ultrasonic probe in accordance with the advancing/retracting actions of the operating rod. Such an arrangement enables the living body tissue to be grasped between the ultrasonic probe and the jaw by performing the closing operation of the jaw. Subsequently, in this state, the ultrasonic vibration is transmitted from the ultrasonic transducer to the ultrasonic probe situated on the treating-section side through the vibration transmitting member. This enables treatment such as incision, excision, coagulation, or the like, of tissue, blood vessels, or the like while coagulating the living body tissue by actions of frictional heat from mechanical vibrations, so as to prevent hemorrhaging.

A larger number of proposals have been made to date with respect to such coagulating cutters, in order to perform more efficiently treatment such as incision, excision, coagulation, or the like, of living body tissue.

For example, Japanese Unexamined Patent Application Publication No. 2002-224133 discloses art relating to an ultrasonic treating device including a treating section of a vibration transmitting member and a grasping section of a jaw for grasping living body tissue, having structures which provide these two components such that they are in uniformly close contact in the jaw-closed state. Such an ultrasonic treating device offers stable coagulation/incision performance.

Also, U.S. Pat. No. 5,322,055 discloses art relating to a device including a blade (probe) formed at the tip end portion of a vibration member having a knife-shaped incision portion and a coagulation face having a substantially arc-shaped cross-section. Furthermore, such an arrangement has a mechanism which enables the operating state to be switched between the state in which the incision portion of the blade is situated so as to face the jaw and the state in which the coagulation face is situated so as to face the jaw. In a case of switching to the state in which the incision portion of the blade is situated so as to face the jaw, the aforementioned device exhibits higher incision performance around the grasped portion of the living body tissue. On the other hand, in a case of switching to the state in which the coagulation face of the blade is situated so as to face the jaw, the aforementioned device exhibits higher coagulation performance around the grasped portion of the living body tissue.

Also, Japanese Unexamined Patent Application Publication No. 8-275951 discloses art relating to a device including a jaw having a coagulation face formed with a large contact area which is to be in contact with living body tissue and an incision portion having a small contact area which is to be in contact with living body tissue. Furthermore, such an arrangement has a mechanism which enables the operating state to be switched between the state in which the incision portion of the jaw is situated so as to face the blade and the state in which the coagulation face of the jaw is situated so as to face the blade. In a case of switching to the state in which the incision portion of the jaw is situated so as to face the blade, the aforementioned device exhibits higher incision performance around the grasped portion of the living body tissue. On the other hand, in a case of switching to the state in which the coagulation face of the jaw is situated so as to face the blade, the aforementioned device exhibits higher coagulation performance around the grasped portion of the living body tissue.

Also, Japanese Unexamined Patent Application Publication No. 2000-254138 discloses art relating to an ultrasonic treating device having a configuration in which a contact portion for coagulating a treated portion grasped between a grasping member and a vibration transmitting member is provided to at least a part of the faces of the aforementioned grasping member and the aforementioned probe, which face each other. Such an arrangement allows the treated portion grasped between the grasping member and the vibration transmitting member to be coagulated when the grasping member, which grasp living body tissue against the probe through the vibration transmitting member, is operated so as to be closed.

SUMMARY OF THE INVENTION

In brief, a coagulating cutter according to the present invention comprises: a transmitting member for transmitting energy, for treating living body tissue, to the living body tissue; an outer sheath through which the transmitting member is passed; and a grasping section supported at the tip end portion of the outer sheath so as to be capable of turning with respect to the transmitting member, which allows the living body tissue to be grasped against the transmitting member. With such an arrangement, upon turning the grasping section toward the transmitting member to be in a closed state, the faces of the transmitting member and the grasping section, which face each other, provide a contact portion, where the transmitting member and the grasping section are in contact with each other over a predetermined length, for incising the living body tissue grasped between the transmitting member and the grasping section, and a non-contact portion, where the transmitting member and the grasping section are provided with a predetermined interval on both sides of the axis extending in the direction of the predetermined length of the contact portion so as not to be in contact with each other, for coagulating the living body tissue.

BRIEF DESCRIPTION OF THE DRAWINGS

FIG. 14 is a side view which shows the configuration of a tip end treating section in a state in which a jaw unit is closed, according to a second embodiment;

FIG. 17 is a side view which shows the configuration of a tip end treating section in a state in which a jaw unit is closed, according to a third embodiment;

DETAILED DESCRIPTION OF THE PREFERRED EMBODIMENTS

Embodiments of the present invention will be described with reference to the drawings.

First Embodiment

Figure 1:
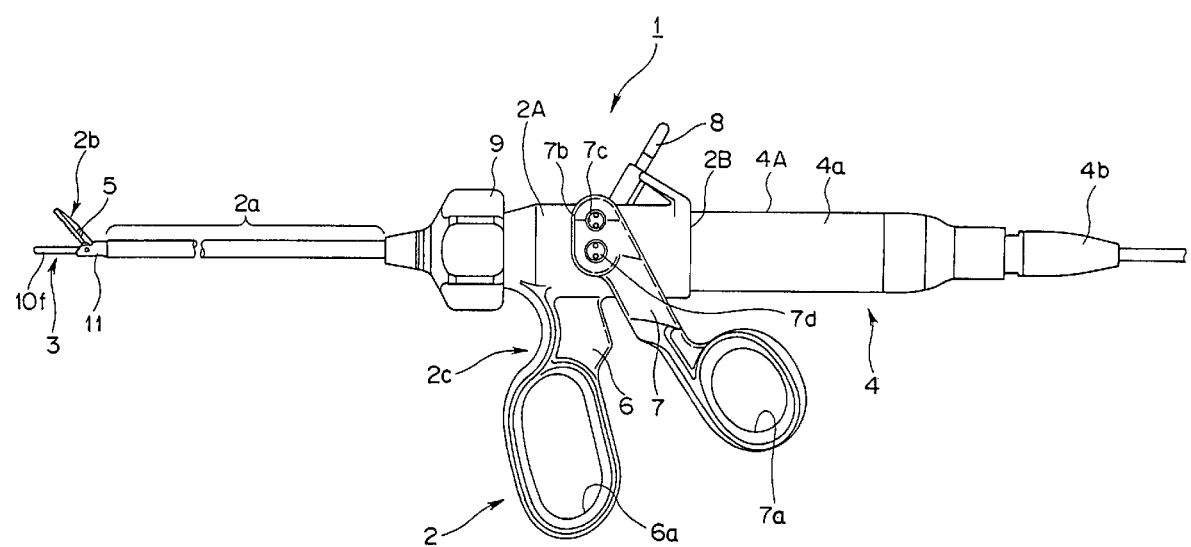
FIG. 1 is a side view of a completely assembled coagulating cutter according to a first embodiment of the present invention.

FIG. 1 is a side view of a completely assembled coagulating cutter according to a first embodiment of the present invention.

Note that with the embodiments according to the present invention, description will be made regarding a case of the device being configured as an ultrasonic coagulating cutter which uses ultrasonic waves as energy to perform treatment such as coagulation, incision, and so forth, of living body tissue.

As shown in FIG. 1, an ultrasonic coagulating cutter 1 according to the first embodiment has three assembly units which can be disassembled into three, i.e., a handle unit 2, a probe unit 3, and a transducer unit 4. These three units 2 through 4 are arranged so as to be assembled into the state shown in FIG. 1.

The transducer unit 4 has a handpiece 4A detachably linked to the handle unit 2. Built into this handpiece 4A is an ultrasonic transducer (not shown) for generating ultrasonic vibrations, within a cylindrical cover 4a covering the perimeter portion of the hand piece 4A.

A horn (not shown) for amplifying the ultrasonic vibrations is connected to the ultrasonic transducer at the tip end side. The tip end side of the horn is arranged so as to be attached to the tip end side of the probe unit 3.

Also, a handpiece cord 4b having a handpiece plug at the end portion (not shown) is connected to the rear end portion of the cylindrical cover 4a.

Figure 2:
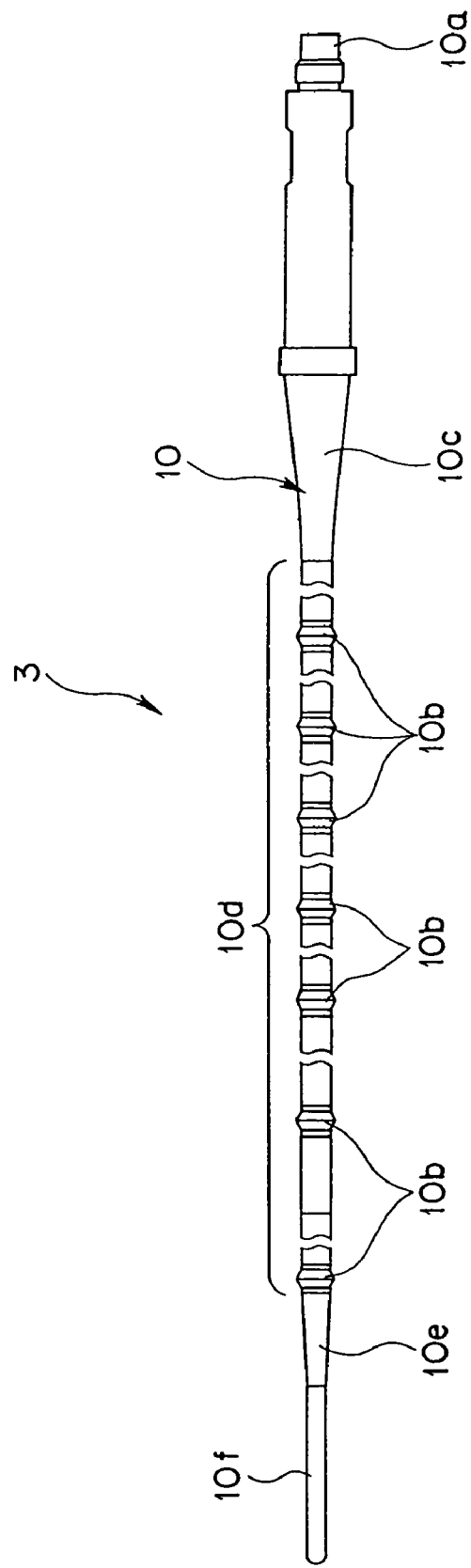
FIG. 2 is a side view which shows the configuration of a probe unit to be inserted into the coagulating cutter shown in FIG. 1.

FIG. 2 is a side view which shows the configuration of a probe unit to be inserted into the coagulating cutter shown in FIG. 1. As shown in FIG. 2, the probe unit 3 has a slender and approximately rod-shaped vibration transmission member 10 detachably linked to the tip end side of the unshown horn within the transducer unit 4. Note that the vibration transmission member 10 makes up a transmission member.

An attaching screw 10a is formed at the base end of the vibration transmission member 10, which allows a connection to be made with a probe attaching portion (unshown) of the unshown horn within the transducer unit 4. The attaching screw 10a is fixed by screwing into a screw hole in the unshown probe attaching portion. Thus, the probe unit 3 and transducer unit 4 are integrally assembled.

As shown in FIG. 2, flanged rubber rings 10b are provided to the vibration transmission member 10 at (multiple) standing wave node positions of the ultrasonic vibrations transmitted from the base end side. The rubber rings 10b are formed ring-shaped of an elastic material for example, and support the vibration transmitting member 10 mounted within a probe channel tube 11b (see FIG. 8) of an insertion sheath portion 2a.

Also, the vibration transmitting member 10 has a base end side horn 10c for second-stage amplification of the ultrasonic vibrations, disposed forward from the second node from the base end side.

Further provided at the tip end side of the base end side horn 10c are an intermediate portion 10d which performs transmission of ultrasonic vibrations, a tip horn 10e which performs final amplification, and a treating section 10f (ultrasonic probe) for treating living body tissue, in that order.

Figure 3:
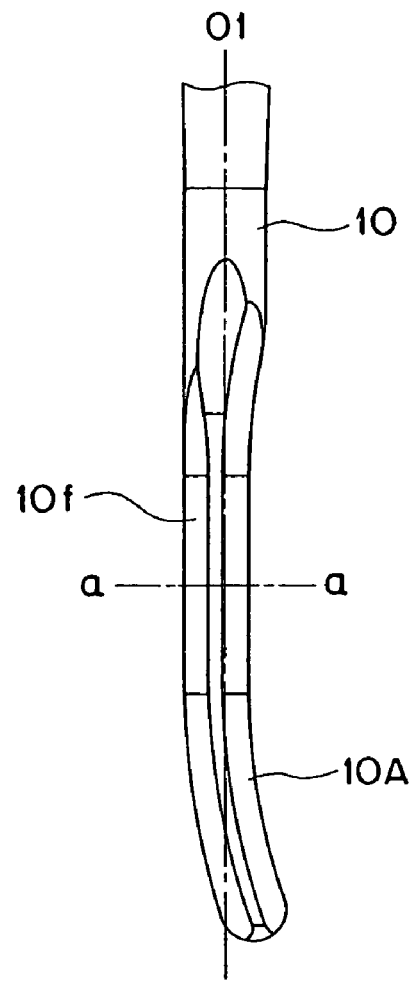
FIG. 3 is a top view which shows a schematic configuration of the vibration transmitting member having a treating section formed in a non-symmetrical shape.
Figure 4:
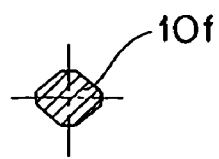
FIG. 4 is a cross-sectional view of the treating section shown in FIG. 3.
Figure 5:
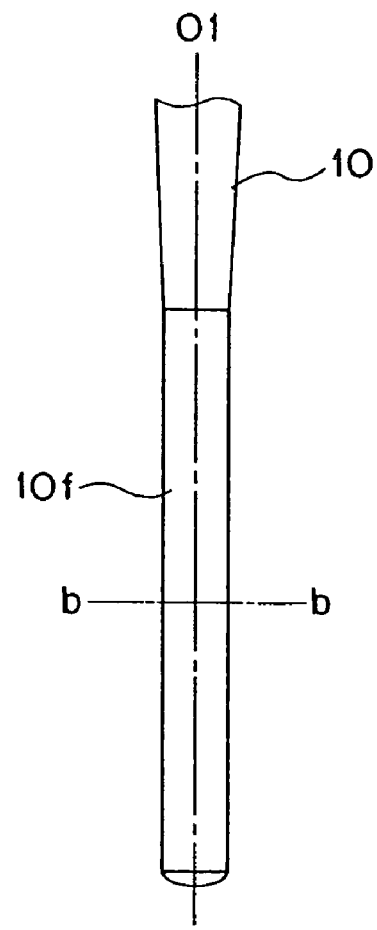
FIG. 5 is a top view which shows the configuration of the vibration transmitting member having the treating section which is formed in a symmetrical shape and which is employed in the first embodiment.
Figure 6:
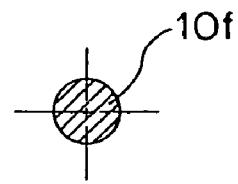
FIG. 6 is a cross-sectional view of the treating section shown in FIG. 5.

FIG. 3 is a top view which shows a schematic configuration of the vibration transmitting member having a treating section formed in a non-symmetrical shape. FIG. 4 is a cross-sectional view of the treating section shown in FIG. 3. FIG. 5 is a top view which shows the schematic configuration of the vibration transmitting member having the treating section which is formed in a symmetrical shape and which is employed in the first embodiment. FIG. 6 is a cross-sectional view of the treating section shown in FIG. 5.

With the present embodiment, the vibration transmitting member 10 provided to the probe unit 3 has the treating section 10f at the tip end side thereof as described above. There are two kinds of the treating sections 10f formed in different shapes, for example.

One of these treating sections 10f is formed in a curved shape departing from the center axis O1, e.g., is configured so as to have a curved portion 10A formed in the shape of an arc, as shown in FIG. 3, for example.

With such an arrangement, the aforementioned treating section 10f is formed in an approximately rectangular cross-section as shown in FIG. 4. The treating section 10f is formed in an approximately rectangular cross-section, and accordingly, the treating section 10f has an edge portion at the lower portion thereof. The edge portion facilitates treatment such as dissection or the like of the living body tissue.

On the other hand, the other treating section 10f is employed in the present embodiment. This treating section 10f is configured in a symmetrical shape with respect to the center axis O1 as shown in FIG. 5. In this case, the treating section 10f is configured in an approximately circular cross-section as shown in FIG. 6. The treating section 10f thus formed in an approximately circular cross-section provides a high insertion capability. Furthermore, such an arrangement allows treatment such as coagulation, incision, and so forth, to be efficiently performed.

While description has been made in the present embodiment regarding the structures of the two kinds of the treating sections 10f, the present invention is not restricted to such an arrangement.

As shown in FIG. 1, the handle unit 2 has a slender insertion sheath portion 2a which is an outer sheath, a tip end action portion 2b disposed at the tip end portion of the insertion sheath portion 2a, and an operating portion 2c disposed at the base end side of the insertion sheath portion 2a.

The operating portion 2c of the handle unit 2 has an approximately cylindrical operating portion body 2A. A transducer connection portion 2B is formed at the base end portion of the operating portion body 2A.

Provided to the outer face of the operating portion body 2A is a fixed handle 6, and a turnable handle 7 capable of turning, making up the operating means. Also, an electrode pin 8 for connecting to high-frequency waves, to which is connected an unshown high-frequency power source, is provided on the upper side of the operating portion body 2A.

The upper side portion of the fixed handle 6 is formed integrally with the cylindrical operating portion body 2A. A fingerhole 6a, through which multiple fingers other than the thumb are selectively passed, is formed at the operating end portion of the fixed handle 6. Furthermore, a thumbhole 7a is provided at the operating end portion of the turnable handle 7, through which the thumb of the same hand can be passed.

Bifurcated linking portions 7b are formed at the upper end side of the turnable handle 7. The bifurcated linking portions 7b are disposed on both sides of the operating portion body 2A. Furthermore, a handle shaft 7c is erected inwards at the upper end portion of each of the bifurcated linking portions 7b. The handle shaft 7c is linked to the operating portion body 2A at a fulcrum positioned above the axial line of the insertion sheath portion 2a. Accordingly, the turnable handle 7 is turnably borne by the handle shaft 7c. Note that a high-frequency insulating cap is provided to the handle shaft 7c.

Also, an action shaft 7d is provided to each of the linking portions 7b of the turnable handle 7 below the handle shaft 7c. This action shaft 7d is for transmitting advancing/retracting force to an operating rod 7e (see FIG. 8) passing through the insertion sheath portion 2a. A later-described jaw unit 5 performs opening/closing operations relative to the treating section 10f due to advancing/retracting actions of the operating rod 7e in the axial direction. Note that the action shaft 7d is disposed approximately on the axial line of the insertion sheath portion 2a.

With the present embodiment, upon the handle of the ultrasonic coagulating cutter 1 being grasped and the turnable handle 7 being closed, the action shaft 7d moves forward, thereby pushing the operating rod 7e forward, such that the jaw unit 5 closes relative to the treating section 10f.

Figure 8:
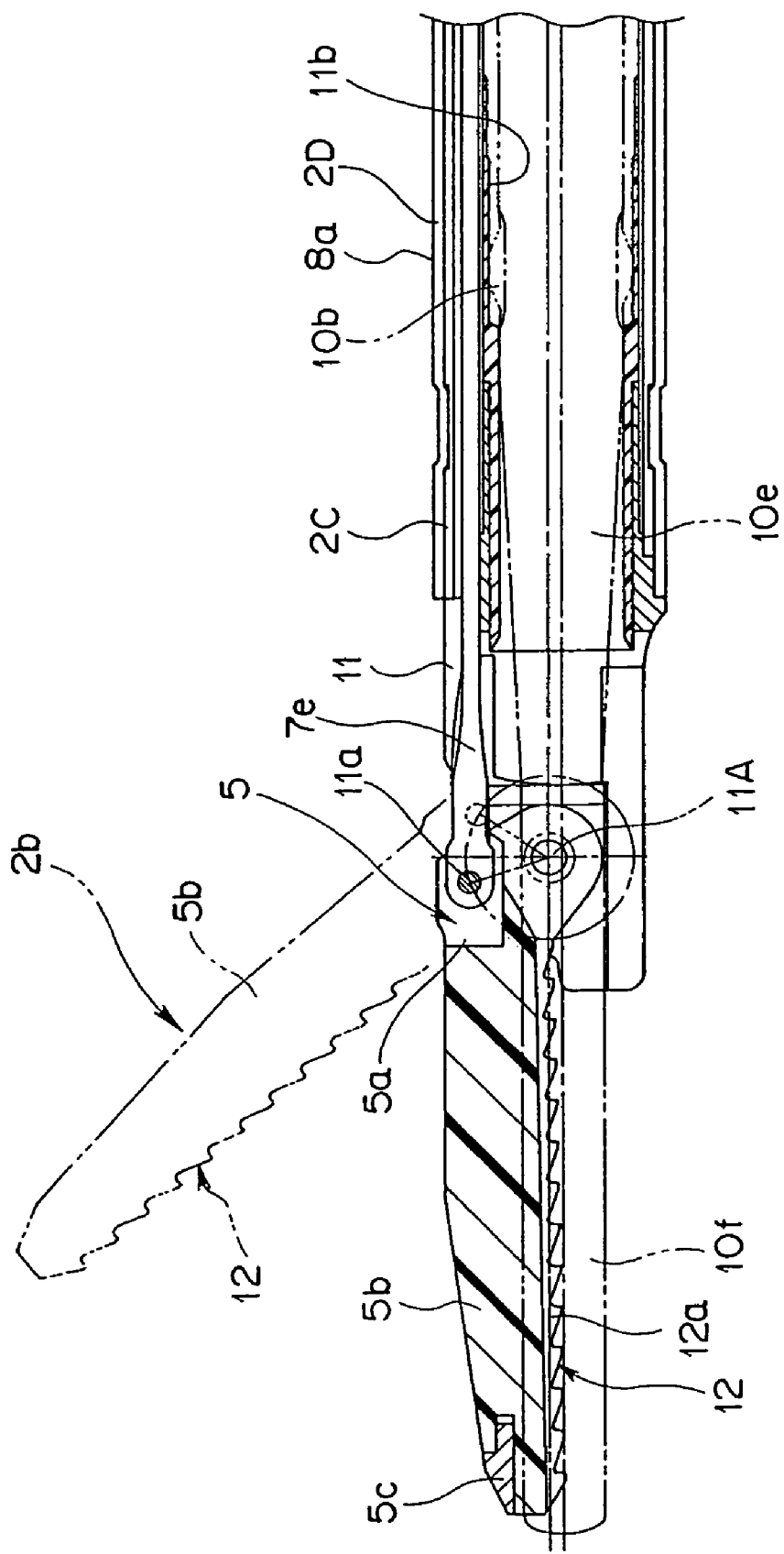
FIG. 8 is a longitudinal cross-sectional view which shows the configuration of the tip end treating section in a jaw unit opened state.

Also, the base end portion of the insertion sheath portion 2a is attached to the tip end portion of the operating portion body 2A along with a rotating knob 9 so as to be capable of axial rotation on the center line of the operating portion body 2A. Here, the insertion sheath portion 2a is formed of an insulating tube 2D mounted on the perimeter of a metal tube 2C as shown in FIG. 8. This insulating tube 2D is provided so as to cover the greater portion of the perimeter of the insertion sheath portion 2a up to the base end portion.

Also, as shown in FIG. 1 and FIG. 8, the handle unit 2 has the single swinging jaw unit 5 for grasping living body tissue provided to the tip end action portion 2b so as to be capable of turning. An operating rod 7e is linked to the jaw unit 5 as described above.

Figure 7:
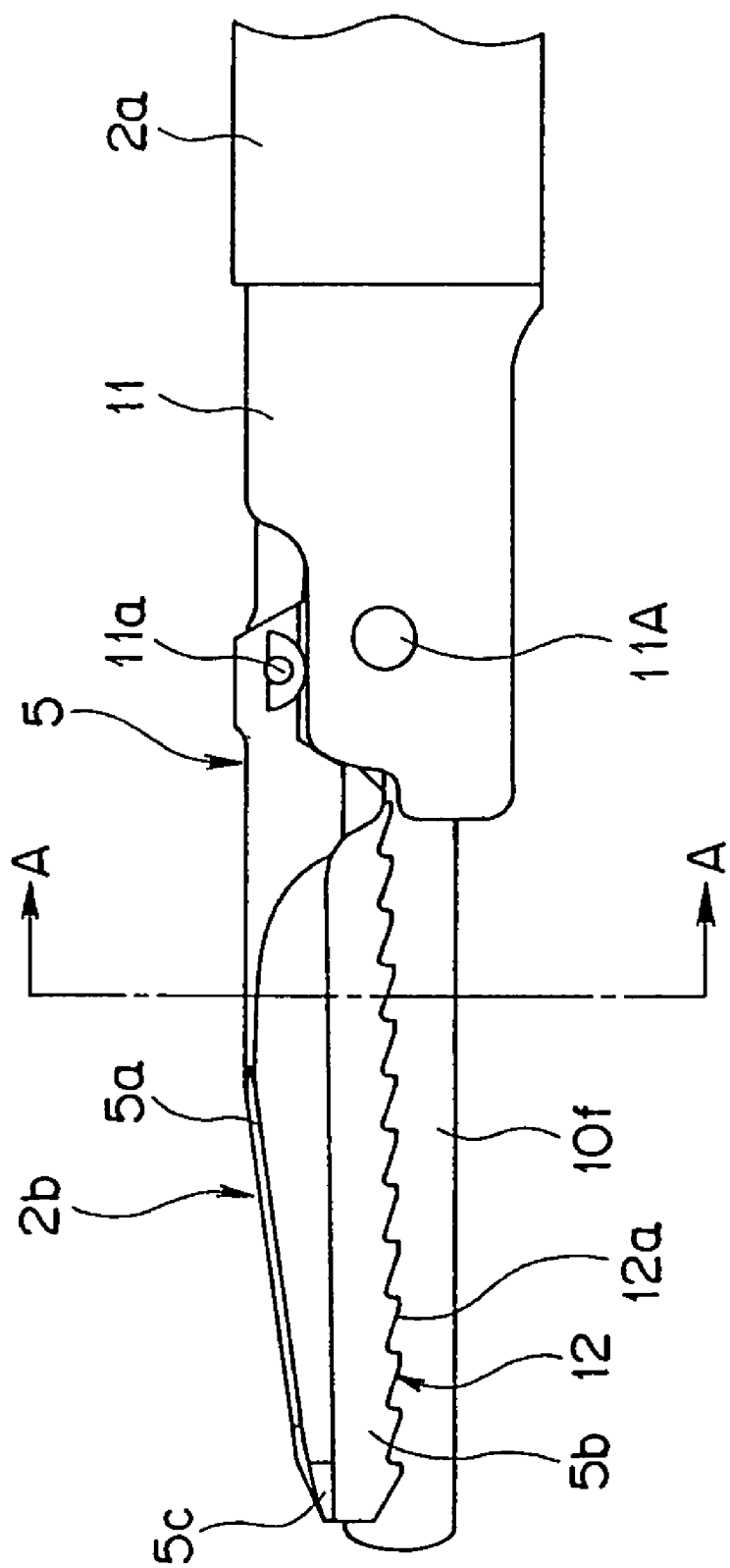
FIG. 7 is a side view which shows the configuration of the tip end treating section in a jaw unit closed state.

Also, as shown in FIG. 1 and FIG. 7, a jaw holding portion 11 for holding the jaw unit 5 is provided to the tip end portion of the insertion sheath portion 2a. The jaw holding portion 11 has the tip end portion of an approximately tube-shaped holding member body covered with an insulating cover (not shown), to effect insulation against high-frequency current.

Next, description will be made regarding the configuration of the jaw unit 5 and vibration transmitting member 10 which are the feature components of the present embodiment with reference to FIG. 7 through FIG. 9.

FIG. 7 is a side view which shows the configuration of the tip end treating section in a jaw unit closed state. FIG. 8 is a longitudinal cross-sectional view which shows the configuration of the tip end treating section in a jaw unit opened state. FIG. 9 is a cross-sectional view along line A-A in FIG. 7.

As shown in FIG. 7 and FIG. 8, the jaw unit 5 has an approximately U-shaped jaw body 5a, a grasping member 5b for grasping living body tissue (blood vessels, organs, etc.), and a grasping section attaching member 5c. Note that the jaw unit 5 and the grasping member 5b of the jaw unit 5 make up a grasping section.

The jaw body 5a has the attaching portion thereof inserted into a slot (not shown) formed on the tip end of the jaw holding portion 11 of the insertion sheath portion 2a, and attached to the jaw holding portion 11 so as to be turnable, with the supporting pin 11A as the turning axis.

Linking pins 11*a* for linking to the operating rod 7*e* are each inserted into the base end portion side of the jaw body 5*a* as shown in FIG. 8.

Also, the grasping member 5*b* is attached to the jaw body 5*a* by way of a grasping member attaching portion 5*c*. The grasping member 5*b* is formed of a low-friction material such as PTFE (Teflon: a registered trademark of DuPont), for example.

Also, a non-slip toothed portion 12 is provided to the side of the grasping member 5*b* facing the living body tissue to be coagulated or incised. Multiple non-slip teeth 12*a* are arrayed on the non-slip toothed portion 12. That is to say, the grasping member 5*b* can grasp the living body tissue to be coagulated or incised against the vibration transmitting member 10 without allowing slipping, due to the non-slip toothed portions 12.

Figure 9:
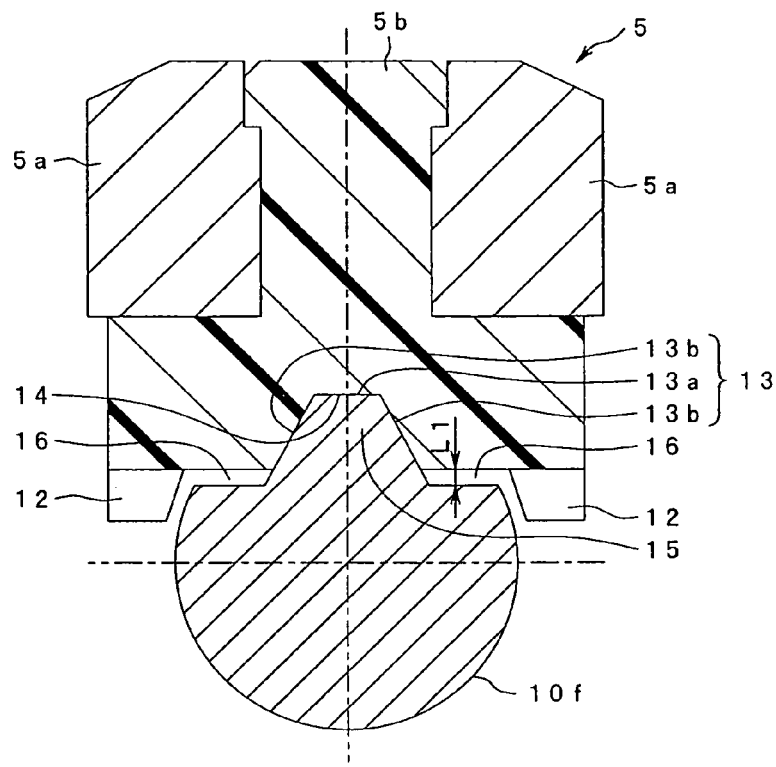
FIG. 9 is a cross-sectional view along line A-A in FIG. 7.

With the present embodiment, as shown in FIG. 9, the treating section 10*f* and the grasping member 5*b* are configured such that the faces thereof facing each other provide a contact portion 13 where these faces are in contact with each other over a predetermined length and which allows living body tissue grasped therebetween to be incised, and a non-contact portion 16 where the aforementioned faces are not in contact with each other over a predetermined length and which allows both sides of the aforementioned living body tissue to be coagulated, when the grasping member 5*b* is turned relative to the vibration transmitting member 10 so as to be in the closed state.

Here, the direction of the aforementioned predetermined length represents the longitudinal direction of the treating section 10*f* and the grasping member 5B. Also, the axis in the direction of the predetermined length represents the axis of the center portion of the treating section 10*f* and the grasping member 5B extending in the longitudinal direction (center line).

As shown in FIG. 9, the contact portion 13 is configured such that at least a part of the faces of the treating section 10*f* and the grasping member 5*b*, which face each other, is formed in a protruding shape when viewed from the insertion direction along which the vibration transmitting member 10 is inserted into the insertion sheath portion 2*a*, so as to permits surface contact between the treating section 10*f* and the grasping member 5*b*.

That is to say, the grasping member 5*b* has a recess 14 in order to provide the contact portion 13 along the center line of a plane orthogonal to a plane across which the treating section 10*f* and the grasping member 5*b* face each other. On the other hand, the treating section 10*f* has a protrusion 15 in order to provide the contact portion 13 along the aforementioned center line, which allows the protrusion 15 to be fit to the recess 14 such that they are in surface contact with each other.

FIG. 9 shows a cross-section in which the treating section 10*f* and the grasping member 5*b* are configured so as to enable these components to be in linear contact with each other. However, the treating section 10*f* and the grasping member 5*b* are configured so as to enable these components to be in surface contact with each other in the longitudinal direction.

Accordingly, upon turning the grasping member 5*b* relative to the vibration transmitting member 10 so as to be in the closed state, the protrusion 15 is fit to the recess 14. This provides the aforementioned contact portion 13 formed of a contact face 13*a* approximately perpendicular to the aforementioned center line and two contact faces 13*b* which are side faces provided to both sides of the contact face 13*a*. Thus, the contact portion 13 offers large grasping force, which is capable of incising living body tissue.

On the other hand, the non-contact portions 16 are provided on both sides of the aforementioned contact portion 13 along the axis thereof extending in the direction of the aforementioned predetermined length. Furthermore, at each of the non-contact portions 16, a gap, which is formed having a predetermined size and which ensures that the treating section 10*f* and the grasping member 5*b* do not come in contact with each other, is formed uniformly along the plane across which the aforementioned treating section 10*f* and the grasping member 5*b* face each other. That is to say, at each of the non-contact portions 16, a gap is formed, having a predetermined size L1 uniformly along the region from both sides of the contact portion 13 to the base end side on the outer sides thereof.

Such a structure provides the non-contact portions 16 with the gap having a uniform size L1, thereby offering a small grasping force, which is suitable for coagulation of living body tissue.

The size L1 of the gap of the aforementioned non-contact portion 16 may be changed as appropriate such that it provides desirable grasping force to be applied to the living body tissue. Note that the size L1 needs to be determined within a range which enables living body tissue grasped within the gap to be coagulated.

The aforementioned contact portion 13 and non-contact portion 16 are formed by machining, for example, at the time of manufacturing the vibration transmitting member 10 and the grasping member 5*b*.

With such a configuration, the aforementioned contact portion 13 provides large grasping force applied to the living body tissue, and the non-contact portion 16 provides small grasping force applied to the living body tissue. This offers an operation in which the non-contact portions 16 coagulate both sides of the living body tissue grasped by the aforementioned contact portion 13 while at the same time incising the living body tissue grasped by the contact portion 13.

Next, the operations of the ultrasonic coagulating cutter 1 according to the present embodiment will be described with reference to FIG. 1 and FIG. 7 through FIG. 9.

At the time of using the ultrasonic coagulating cutter 1 according to the present embodiment, a surgeon grips the fixed handle 6 of the handle unit 2, and operates the turnable handle 7. In response to the operations of the turnable handle 7, the operating rod 7*e* advances/retracts within the insertion sheath portion 2*a*, and the jaw body 5*a* to which the grasping member 5*b* of the tip end action portion 2*b* has been attached is opened and closed.

Now, in the event of operating the turnable handle 7 so as to grasp (closing operation), the action shaft 7*d* revolves around the handle shaft 7*b* in the clockwise direction in FIG. 1. In response to the action shaft 7*d* proceeding in an approximately linear direction toward the tip end side, the operating rod 7*e* within the insertion sheath portion 2*a* is pressed toward the tip end side, and the jaw unit 5 is completely closed, in a state in which the grasping member 5*b* of the jaw unit 5 is pressed against the treating section 10*f* of the vibration transmitting member 10, as indicated by the solid line in FIG. 8.

Also, for operations for opening the turnable handle 7 from a completely closed position, the action shaft 7*d* revolves around the handle shaft 7*b* in the counterclockwise direction in FIG. 1. The moving of the action shaft 7*d* at this time retracts the operating rod 7*e* backwards.

Accordingly, due to the operating rod 7*e* retreating through the insertion sheath portion 2*a* in the direction parallel to the center axis of the insertion sheath portion 2*a*, the grasping member 5*b* of the jaw unit 5 circles in the direction away from the vibration transmitting member 10, i.e., the jaw unit 5 turns clockwise with the supporting pin 11A as a turning axis, and opens relative to the treating section 10f of the vibration transmitting member 10, as indicated by the imaginary line in FIG. 7.

Thus, with the ultrasonic coagulating cutter 1, the surgeon performs a turning operation of the turnable handle 7 to turn the jaw unit 5 relative to the treating section 10f of the vibration transmitting member 10, which is situated at a fixed position, thereby grasping living body tissue between the treating section 10f and the grasping member 5b. Furthermore, such an arrangement provides treatment such as dissection and so forth of the living body tissue with the aforementioned treating section 10f and grasping member 5b by opening the jaw unit 5.

Now, let us say that the surgeon performs treatment such as coagulation and incision of the living body tissue using the ultrasonic coagulating cutter 1 having such functions.

The surgeon grips so as to close the turnable handle 7 (closing operation) as described above, whereby the jaw unit 5 is turned to a fully closed state, relative to the treating section 10f of the vibration transmitting member 10, which is at a stationary position. As a result, the living body tissue is grasped between the treating section 10f which is an ultrasonic probe of the vibration transmitting member 10 and the grasping member 5b of the jaw unit 5.

In this case, with regard to the grasping force applied to the living body tissue grasped between the treating section 10f of the vibration transmitting member 10 and the grasping member 5b of the jaw unit 5, the contact portion 13 provides large grasping force, and the non-contact portion 16 provides small grasping force. In this state, ultrasonic waves are supplied to the aforementioned vibration transmitting member 10.

As a result, frictional heat generated due to the ultrasonic waves is applied to the living body tissue grasped between the treating section 10f and the grasping member 5b, thereby effecting coagulation and incision of the living body tissue.

With the present embodiment, the non-contact portion 16 provides small grasping force. This reduces ultrasonic wave transmission performance, thereby producing reduced frictional heat.

Accordingly, the living body tissue grasped by the non-contact portion 16 does not reach the temperature which results in incision of the living body tissue. Thus, the living body tissue is coagulated.

At the same time as the coagulation of the living body tissue by the aforementioned non-contact portion 16, the contact portion 13 provides large grasping force. This increases ultrasonic wave transmission performance, thereby producing ample frictional heat therearound. Accordingly, the living body tissue grasped by the contact portion 13 is coagulated and incised.

As described above, the present embodiment provides the contact portion 13 where the treating section 10f and the grasping member 5b are in contact with each other and the non-contact portions 16, which are provided on both sides of the contact portion 13, and where the treating section 10f and the grasping member 5b are not in contact with each other, in the state in which the grasping portion 5b is closed after having been turned relative to the vibration transmitting member 10. Note that each of the contact portion 13 and the non-contact portions 16 is provided on a plane across which the treating section 10f and the grasping member 5b face each other. Such an arrangement enables the living body tissue grasped by the contact portion 13 to be incised and coagulated while coagulating the living body tissue grasped by the non-contact portions 16 situated on both sides of the contact portion 13.

With the conventional technique disclosed in Japanese Unexamined Patent Application Publication No. 2000-254138, particularly, in a case of coagulation and incision of blood vessels, the surgeon needs to perform troublesome operation as follows. That is to say, first, the surgeon coagulates the blood vessel using the non-contact portion. Then, the surgeon shifts the contact portion to the blood vessel to be incised. Subsequently, the surgeon performs incision and coagulation of the blood vessel using the contact portion. In contrast with such a conventional technique, the ultrasonic coagulating cutter 1 according to the present embodiment enables living body tissue such as blood vessels and so forth to be coagulated and incised at the same time with high efficiency in a short period of time without involving such troublesome operation.

Furthermore, in a case of treatment of blood vessels within the body using the ultrasonic coagulating cutter 1 according to the present embodiment, the portion of the blood vessel grasped by the contact portion 13 can be incised and coagulated (for stanching the flow of blood) and the portions of the blood vessel grasped by the non-contact portions 16 situated on both sides of the contact portion 13 can be coagulated (for stanching the flow of blood) at the same time. Such an arrangement provides incision of the blood vessel while coagulating the blood vessel (for stanching the flow of blood). This enables treatment of blood vessels to be performed in a sure manner, with high efficiency, and in a short period of time.

Note that the treating section 10f of the vibration transmitting member 10 and the grasping member 5b of the jaw unit 5 according to the present embodiment may be configured so as to provide the contact portion 13 and the non-contact portions 16 according to a first modification through a fourth modification as described below.

Description will be made regarding the first modification through fourth modification with reference to FIG. 10 through FIG. 13. Note that FIG. 10 through FIG. 13 are cross-sectional views along line A-A in FIG. 7.

(First Modification)

Figure 10:
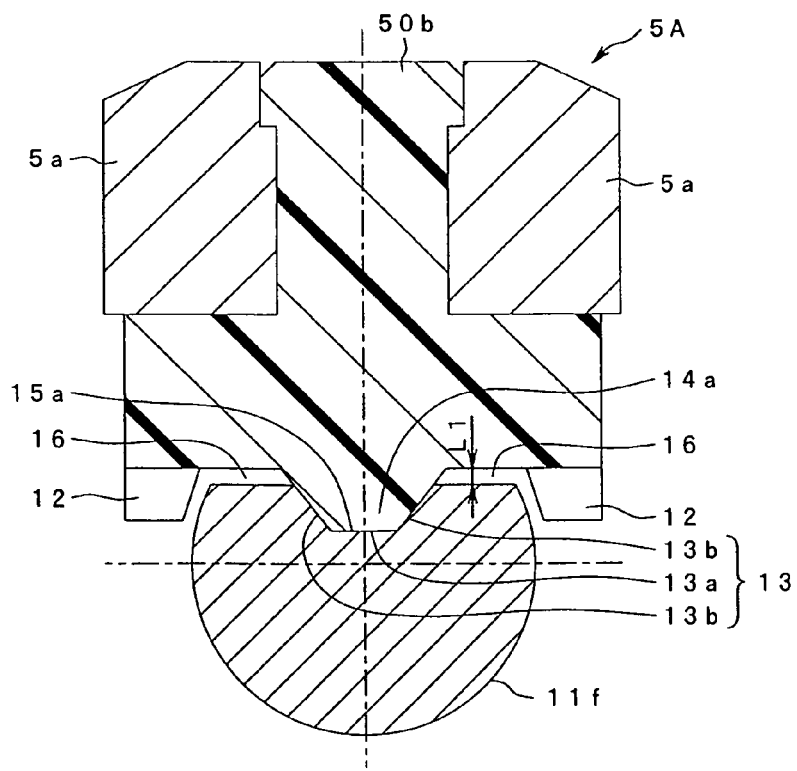
FIG. 10 is a cross-sectional view which shows the configuration of the tip end treating section according to a first modification of the first embodiment.

FIG. 10 is a cross-sectional view which shows the configuration of the tip end treating section according to a first modification of the first embodiment.

As shown in FIG. 10, with the first modification, the aforementioned contact portion 13 is configured such that the protrusion 15 and the recess 14, which are components thereof, are arranged in the opposite order (in the vertical direction) of the arrangement according to the first embodiment.

That is to say, the grasping member 50b of the jaw unit 5A has a protrusion 14a provided so as to protrude downward, thereby providing the contact portion 13 on a center line of a plane perpendicular to a plane across which the treating section 10f and the grasping member 5b face each other (center line of the cross-section of the treating section 10f and the grasping member 5b), for example.

On the other hand, the treating section 11f of the vibration transmitting member 10 has a recess 15a which provides the contact portion 13 on the aforementioned center line, and which can be caused to be in surface contact with the aforementioned protrusion 14a by being fit thereto.

Note that the non-contact portions 16 are provided by the combination of the structures of the protrusion 14a and the recess 15a, which form the aforementioned contact portion 13, generally in the same way as with the first embodiment. The other components are the same as those of the first embodiment.

The aforementioned first modification having such a configuration has the same functions and advantages as those of the first embodiment.

(Second Modification)

Figure 11:
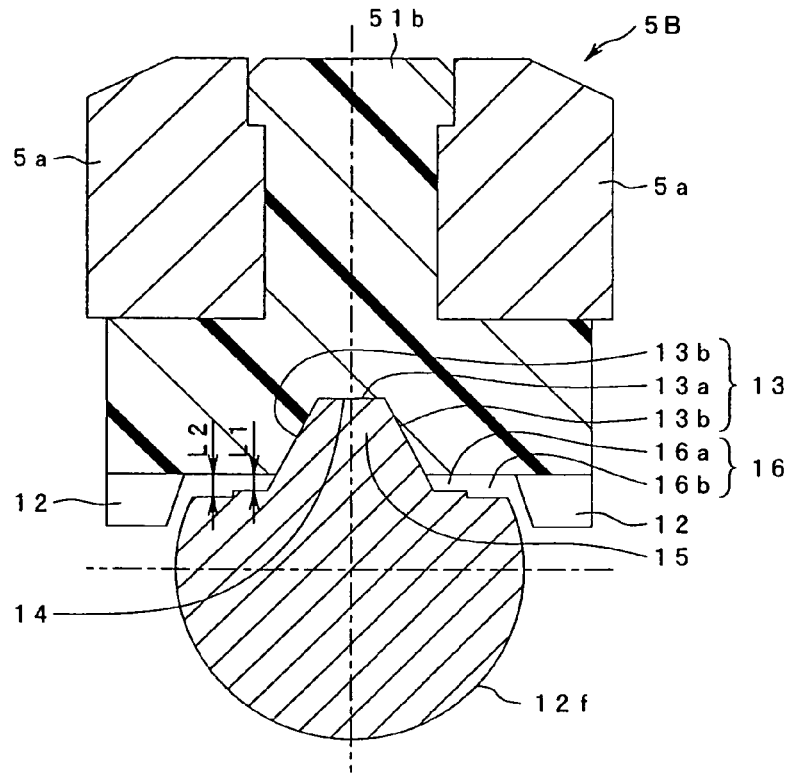
FIG. 11 is a cross-sectional view which shows the configuration of the tip end treating section according to a second modification of the first embodiment.

FIG. 11 is a cross-sectional view which shows the configuration of the tip end treating section according to a second modification of the first embodiment.

As shown in FIG. 11, the structures of the protrusion 15 and the recess 14 forming the aforementioned contact portion 13 according to the second modification are the same as those of the first embodiment. On the other hand, with regard to the gap which provides each of the non-contact portions 16 with a predetermined size, the size of the gap increases in a stepped manner according to the distance from the aforementioned protrusion 15 and both sides of the aforementioned recess 14.

For example, the non-contact portion 16 has a first gap 16a formed with approximately the same size L1 as that of the first embodiment and a second gap 16b formed with a greater size than L1 from the outer side of the first gap 16a to the base end.

That is to say, the treating section 12f of the vibration transmitting member 10 has two-stepped structures extending from both sides of the protrusion 15 to the base ends, so as to provide the aforementioned first gaps 16a and second gaps 16b at the time of closing the jaw unit 5B relative to the vibration transmitting member 10.

The other components are the same as those of the first embodiment.

With the non-contact portion 16 according to the second modification, the second gap 16b has a greater size than that of the first gap 16a, thereby exhibiting smaller grasping force. That is to say, the second gap 16b provides smaller ultrasonic wave transmission performance than that of the first gap 16a, thereby generating reduced frictional heat.

Thus, in a case of coagulating living body tissue using the non-contact portion 16, the aforementioned first gap 16a coagulates the living body tissue in a sure manner, and at the same time the second gap 16b situated on the outer sides of the first gap 16a, coagulates the living body tissue with smaller coagulating force than that of the first gap 16a. It is needless to say that the contact portion 13 enables the living body tissue to be incised at the same time.

The other functions and advantages are the same as those of the first embodiment.

(Third Modification)

Figure 12:
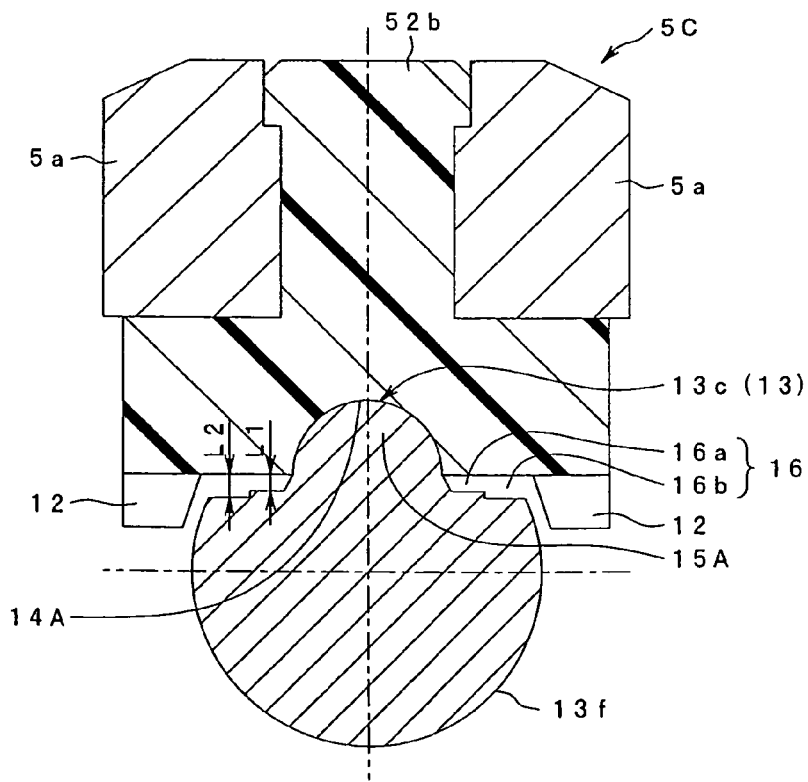
FIG. 12 is a cross-sectional view which shows the configuration of the tip end treating section according to a third modification of the first embodiment.

FIG. 12 is a cross-sectional view which shows the configuration of a tip end treating section according to a third modification of the first embodiment.

As shown in FIG. 12, the third modification has an improved configuration from that of the aforementioned second modification. Specifically, with regard to the third modification, while the non-contact portion 16 has the same structure as that according to the second modification, the protrusion 15 and the recess 14, which provide the contact portion 13, are formed in an arc-shaped cross-section, instead of the rectangular cross-section employed in the first embodiment, first modification, and second modification.

That is to say, the grasping member 52b of the jaw unit 5C has a recess 14A formed in an arc-shaped cross-section, so as to protrude toward the treating section 13f, thereby providing the contact portion 13 on the center line of a plane perpendicular to the plane across which the treating section 13f and the grasping member 52b face each other. On the other hand, the treating section 13f of the vibration transmitting member 10 has a protrusion 15A which can be caused to be in surface contact with the aforementioned recess 14A by being fitting thereof, thereby providing the contact portion 13 on the aforementioned center line.

Note that the non-contact portions 16 are provided by the combination of the structures of the protrusion 15A and the recess 14A, which form the aforementioned contact portion 13, in generally the same way as with the second modification. The other components are the same as those of the first embodiment.

The aforementioned third modification having such a configuration provides the same functions and advantages as those of the second modification. In addition, the contact face 13c of the contact portion 13 is formed in an arc-shaped cross-section. Thus, particularly, in a case that the living body tissue to be treated is a blood vessel, such an arrangement allows the blood vessel to be suitably grasped. This increases the coagulation performance, thereby offering highly-efficient incision.

(Fourth Modification)

Figure 13:
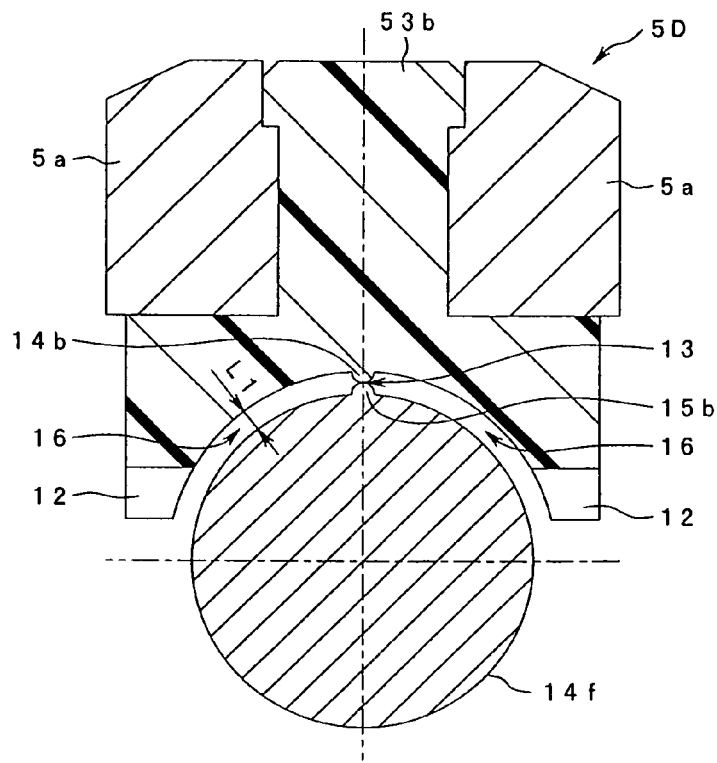
FIG. 13 is a cross-sectional view which shows the configuration of the tip end treating section according to a fourth modification of the first embodiment.

FIG. 13 is a cross-sectional view which shows the configuration of a tip end treating section according to a fourth modification of the first embodiment.

As shown in FIG. 13, the contact portion 13 according to the fourth modification has a configuration including a combination of two protrusions 14b and 15b arranged on the center line of a curved plane across which the faces of the treating section 14f and a grasping member 53b face each other, which has arc-shaped cross sections with the same curvature (on the center line of the cross-section of the treating section 14f and the grasping member 53b with respect to the longitudinal direction), instead of a combination of protrusion and recess structures. Note that the aforementioned curved plane has the same curvature as that of the faces of the treating section 14f and the grasping member 53b which face each other.

Specifically, the grasping member 53b of the jaw unit 5D is configured such that the inner face (grasping face) is formed in the shape of a recess having an arc-shaped cross-section such that it extends in the direction of the predetermined length (longitudinal direction). Furthermore, the protrusion 14b is provided to the aforementioned inner face on the center line of a plane perpendicular to a plane across which the treating section 15f and the grasping member 53b face each other. The protrusion 14b is formed so as to extend over the entire region in the longitudinal direction, and so as to protrude toward the treating section 14f, thereby providing the contact portion 13.

On the other hand, the treating section 14f of the vibration transmitting member 10 is formed in a cylindrical shape. The outer face thereof is formed in an arc-shaped cross-section with the same curvature as that of the aforementioned inner face (grasping face) of the grasping member 53b, for example. Furthermore, a protrusion 15b is provided on the center axis of the outer face of the treating section 14f, which can be caused to be in contact with the aforementioned protrusion 14b so as to be in surface contact therewith, thereby providing the contact portion 13.

Note that such a configuration provides the non-contact portions 16 having a gap with a size L1 which is approximately uniform over the region extending from both sides of the protrusion 14b and the protrusion 15b, which form the aforementioned contact portion 13. Furthermore, the gap is formed corresponding to the curvature of the inner face of the grasping member 53b (grasping face) and the outer face of the treating section 14f, each of which is formed in an arc-shaped cross-section.

Furthermore, at least one of the protrusion 14*b* and the protrusion 15*b* of the aforementioned contact portion 13 is not restricted to an arrangement as shown in FIG. 13. For example, the protrusion protruding from the treating section 14*f* or the grasping member 53*b* may be formed with a different height as appropriate. Also, one of these protrusions may be formed with an increased width along the outer face of the treating section 14*f* so as to increase the grasping force and the contact area.

The other components are the same as those of the first embodiment.

The fourth modification provides a smaller contact area, where the protrusion 14*b* and the protrusion 15*b* of the contact portion 13 are in contact with each other, than that of the first embodiment. This allows the living body tissue to be incised with a reduced incision width. Furthermore, the fourth modification provides the non-contact portions 16 having a gap formed with a greater length in the outer-face direction of the treating section 14*f* than that of the first embodiment. This allows both sides of the incised living body tissue portion to be coagulated with an increased width.

Thus, an arrangement according to the fourth modification is particularly effective in a case in which the living body tissue is to be incised with a small width and both sides of this incised portion is to be coagulated over a large width. The other functions and advantages are the same as those of the first embodiment described above.

As described above, the ultrasonic coagulating cutter 1 according to the first embodiment may be configured using any one of the configurations of the first modification through fourth modification as described above. In any of these cases, such an arrangement provides efficient simultaneous coagulation and incision of living body tissue.

Second Embodiment

Figure 15:
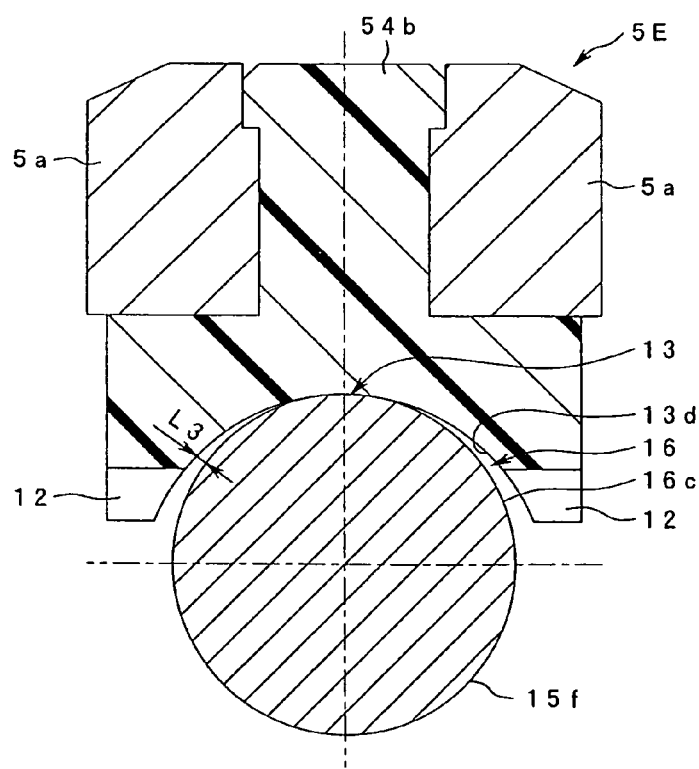
FIG. 15 is a cross-sectional view along line A-A in FIG. 14.

Next, description will be made regarding an ultrasonic coagulating cutter according to a second embodiment of the present invention with reference to FIG. 14 and FIG. 15. FIG. 14 is a side view which shows the configuration of a tip end treating section in a state in which a jaw unit is closed, according to the second embodiment. FIG. 15 is a cross-sectional view along line A-A in FIG. 14.

In the ultrasonic coagulating cutter 1 according to the present embodiment, at least one of the inner face (grasping face) of a grasping member 54*b* and the outer face (grasping face) of the treating section 15*f* is formed in an arc-shaped cross-section such that the treating section 15*f* and the grasping member 54*b* are in contact with each other when viewed from the insertion direction along which the vibration transmitting member 10 is to be inserted into the insertion sheath portion 2*a*.

Specifically, as shown in FIG. 14, the ultrasonic coagulating cutter 1 according to the present embodiment includes a jaw unit 5E having the grasping member 54*b* and the vibration transmitting member 10 having the treating section 15*f*.

As shown in FIG. 15, the grasping member 54*b* of the jaw unit 5E is formed such that the inner face (grasping member) 13*d* extending along the longitudinal direction is a recessed portion having an arc-shaped cross-section. That is to say, the grasping member 54*b* has an arc-shaped cross-section.

On the other hand, the treating member 15*f* of the vibration transmitting member 10 is formed in a cylindrical shape. Furthermore, the outer face 16*c* thereof is formed in an arc-shaped cross section having a smaller curvature than that of the aforementioned inner face (grasping face) 13*d* of the grasping member 54*b* formed in an arc-shaped cross-section.

In other words, the grasping member 54*b* is formed in an arc-shaped cross-section with a greater curvature than that of the treating section 15*f*.

Also, the grasping member 54*b* and the treating section 15*f* may be formed in arc-shaped cross sections with different curvatures. Also, the grasping member 54*b* or the treating section 15*f* may be formed in a part of a circular cross-section on a plane across which the grasping member 54*b* and the treating section 15*f* face each other. Also, the grasping member 54*b* or the treating section 15*f* may be formed in a part of an ellipsoid cross-section.

With the present embodiment, the treating section 15*f* has an arc-shaped cross-section. Furthermore, the grasping member 54*b* has an arc-shaped cross-section with a greater curvature than that of the treating section 14*f*. Such an arrangement provides the contact portion 13 and the non-contact portions 16 between the treating section 15*f* and the grasping member 54*b* when the jaw unit 5E is in a fully closed state.

Thus, the contact portion 13 has the contact portion 13*d* where the outer face 16*c* of the treating member 15*f* and the grasping member 54*b* can be in contact with each other.

On the other hand, the non-contact portion 16 is formed such that the size L3 of the gap formed at the non-contact portion 16 increases according to the increase in the distance from the axis in the predetermined length direction along a plane across which the treating section 15*f* and the grasping member 54*b* face each other, i.e., the center axis extending in the longitudinal direction of the treating section 16*f* and the grasping member 54*b*.

The other components are the same as those of the first embodiment.

Next, description will be made regarding the operations of the ultrasonic coagulating cutter 1 according to the second embodiment with reference to FIG. 14 and FIG. 15.

Now, let us say that a surgeon performs treatment such as coagulation and incision of living body tissue using the ultrasonic coagulating cutter 1 having such functions.

The surgeon grips so as to close the turnable handle 7 (closing operation) in the same way as in the first embodiment, whereby the jaw unit 5E is turned to a fully closed state, relative to the treating section 15*f* of the vibration transmitting member 10, which is at a stationary position, as shown in FIG. 14. As a result, the living body tissue is grasped between the treating section 15*f* which is an ultrasonic probe of the vibration transmitting member 10 and the grasping member 54*b* of the jaw unit 5E.

In this case, with regard to the grasping force applied to the living body tissue grasped between the treating section 15*f* of the vibration transmitting member 10 and the grasping member 54*b* of the jaw unit 5E, the contact portion 13 between the treating section 15*f* and the grasping member 54*b* provides large grasping force, and the non-contact portion 16 therebetween provides small grasping force. In this state, ultrasonic waves are supplied to the aforementioned vibration transmitting member 10.

As a result, frictional heat generated due to the ultrasonic waves is applied to the living body tissue grasped between the treating section 15*f* and the grasping member 54*b*, thereby effecting coagulation and incision of the living body tissue.

With the present embodiment, the non-contact portion 16 provides small grasping force. This reduces ultrasonic wave transmission performance, thereby producing reduced frictional heat. Accordingly, the living body tissue grasped by the non-contact portion 16 does not reach the temperature which results in incision of the living body tissue. Thus, the living body tissue is coagulated.

With regard to the non-contact portion 16 according to the present embodiment, the size L3 of the gap increases according to the increase in the distance from the center axis in the longitudinal direction of the treating section 15f and the grasping member 54b. Accordingly, the grasping force becomes gradually smaller with the increase in the distance from the aforementioned center axis. Accordingly, the ultrasonic vibration transmission performance becomes gradually smaller with the increase in the distance from the aforementioned center axis. As a result, the degree of coagulation of the grasped living body tissue becomes smaller with the increase in the distance from the aforementioned center axis.

At the same time as the coagulation of the living body tissue by the aforementioned non-contact portions 16, the contact portion 13 produces ample frictional heat due to its high ultrasonic vibration transmission performance since grasping force is large. Accordingly, the living body tissue grasped by the contact portion 13 is coagulated and incised.

Thus, the present embodiment has the advantage of enabling the non-contact portions 16 to coagulate the living body tissue in such a manner that the degree of coagulation of the living body tissue decreases with the increase in the distance from the incised portion, in addition to the same advantages of the first embodiment.

Note that the treating section 15f of the vibration transmitting member 10 according to the present embodiment may be configured so as to provide the contact portion 13 and the non-contact portions 16 according to a first modification described below.

Description will be made regarding the first modification with reference to FIG. 16. Note that FIG. 16 is a cross-sectional view along line A-A in FIG. 14.

(First Modification)

Figure 16:
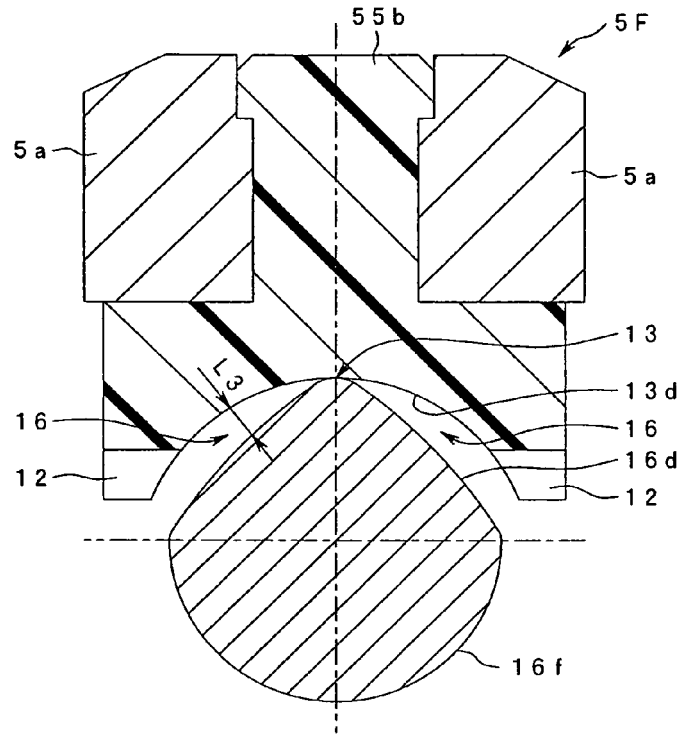
FIG. 16 is a cross-sectional view which shows the configuration of a tip end treating section according to a first modification of the second embodiment.

FIG. 16 is a cross-sectional view which shows the configuration of a tip end treating section according to the first modification of the second embodiment.

As shown in FIG. 16, the treating section 16f of the vibration transmitting member 10 according to the first modification is configured such that a part providing the contact portion 13 is formed in an arc-shaped cross-section and a part providing the non-contact portions 16 is formed in an ellipsoid cross-section.

That is to say, the treating section 16f is formed such that the outer face 16d on the center line of the cross-section thereof on the side facing the grasping member 55b is formed in an arc-shaped cross-section. Furthermore, a part of the outer face 16d situated on both sides of the aforementioned part formed in an arc-shaped cross-section are formed in an ellipsoid cross-section.

Note that the outer face 16d formed in an ellipsoid cross-section may be formed with an appropriately adjusted curvature.

Thus, the first modification provides the non-contact portions 16 having gaps formed such that the size of the gaps L3 increases with the increase in the distance from the axis extending in the predetermined length direction along a plane across which the treating section 16f and the grasping member 55b face each other, i.e., the center axis extending in the longitudinal direction of the treating section 15f and the grasping member 54b.

Note that, in a case that the first modification is configured with the outer face 16d having an ellipsoid cross-section with an unsuitable curvature, the aforementioned size of the gaps L3 becomes gradually smaller with the increase in the distance from the aforementioned center axis. Accordingly, the first modification is preferably configured with the outer face 16d having a curvature such that the aforementioned size of the gaps L3 becomes greater with the increase in the distance from the aforementioned center axis.

The first modification includes the jaw unit 5F and the grasping member 55b, and the other components are the same as those of the second embodiment.

Thus, the first modification provides the same functions and advantages as those of the second embodiment described above.

Third Embodiment

Figure 18:
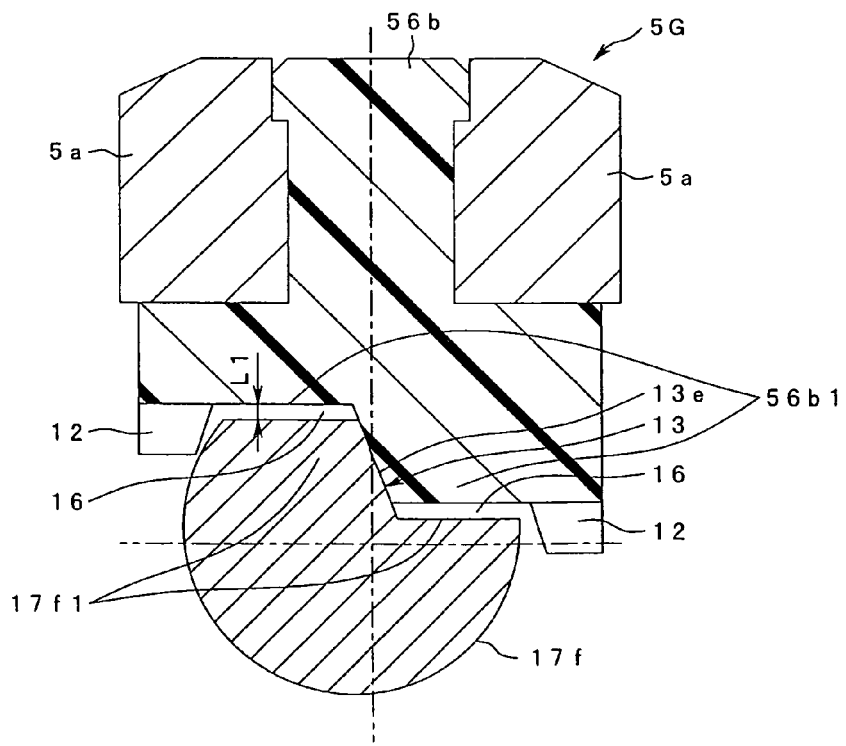
FIG. 18 is a cross-sectional view along line A-A in FIG. 17.

Next, description will be made regarding an ultrasonic coagulating cutter according to a third embodiment of the present invention with reference to FIG. 17 and FIG. 18. FIG. 17 is a side view which shows the configuration of a tip end treating section in a state in which a jaw unit is closed, according to the third embodiment. FIG. 18 is a cross-sectional view along line A-A in FIG. 17.

In the ultrasonic coagulating cutter 1 according to the present embodiment, stepped portions 17f1 and 56b1 are formed on the faces of the treating section 17f of the vibration transmitting member 10 and the grasping member 56b facing each other so as to allow the treating section 17f and the grasping member 56b to be in surface contact with each other, when viewed from the insertion direction along which the vibration transmitting member 10 is to be inserted into the insertion sheath portion 2a.

Specifically, as shown in FIG. 17, the ultrasonic coagulating cutter 1 according to the present embodiment includes a jaw unit 5G having the grasping member 56b and the vibration transmitting member 10 having the treating section 17f.

As shown in FIG. 18, the grasping member 56b of the jaw unit 5G has the stepped portion 56b1 on the face thereof facing the treating section 17f, which allows the treating section 17f and the grasping member 56b to be caused to be in surface contact with each other at the center of a plane across which the treating section 17f and the grasping member 56b face each other.

That is to say, the grasping member 56b has a contact face 13e around the center axis of the cross-section thereof. Furthermore, the grasping member 56b has the stepped portions 56b1 formed of an upper face and a lower face provided to both sides of the contact face 13e such that they extend in the longitudinal direction.

On the other hand, the treating section 17f of the vibration transmitting member 10 has the stepped portion 17f1 on the face thereof facing the grasping member 56b, which allows the treating section 17f and the grasping member 56b to be caused to be in surface contact with each other at the center of a plane across which the treating section 17f and the grasping member 56b face each other.

That is to say, the treating section 17f has a contact face 13e around the center axis of the cross-section thereof, in the same way as described above. Furthermore, the treating section 17f has the stepped portions 17f1 formed of an upper face and a lower face provided to both sides of the contact face 13e such that they extend in the longitudinal direction.

Note that the aforementioned stepped portions 56b1 and 17f1 may be formed with a height adjusted as desired corresponding to the kind of the living body tissue to be coagulated and incised. Also, the contact area and the degree of inclination of the contact face 13e may be adjusted as desired corresponding to the kind of the living body tissue to be incised.

With the present second embodiment as described above, the treating section 17f and the grasping member 56b have the stepped portions 56b1 and 17f1 formed so as to allow the treating section 17*f* and the grasping member 56*b* to be caused to be in surface contact with each other at the center of a plane across which the treating section 17*f* and the grasping member 56*b* face each other. Thus, the second embodiment provides the contact portion 13 and the non-contact portions 16 between the treating section 17*f* and the grasping member 56*b* when the jaw unit 5G is in a fully closed state, in the same way as with the first embodiment.

Thus, the contact portion 13 has the contact face 13*e* which allows the treating section 15*f* and the grasping member 54*b* to be caused to be in surface contact with each other.

On the other hand, the non-contact portions 16 are provided so as to have gaps of a predetermined size L1, which is uniform over the aforementioned stepped portions 56*b*1 and 17*b*1 provided on a plane across which the treating section 15*f* and the grasping member 54*b* face each other.

The other components are the same as those of the first embodiment.

Next, description will be made regarding the operations of the ultrasonic coagulating cutter 1 according to the third embodiment with reference to FIG. 17 and FIG. 18.

Now, let us say that a surgeon performs treatment such as coagulation and incision of living body tissue using the ultrasonic coagulating cutter 1 having such functions.

The surgeon grips so as to close the turnable handle 7 (closing operation) in the same way as in the first embodiment, whereby the jaw unit 5G is turned to a fully closed state, relative to the treating section 17*f* of the vibration transmitting member 10, which is at a stationary position, as shown in FIG. 17. As a result, the living body tissue is grasped between the treating section 17*f* which is an ultrasonic probe of the vibration transmitting member 10 and the grasping member 56*b* of the jaw unit 5G.

In this case, with regard to the grasping force applied to the living body tissue grasped between the treating section 17*f* of the vibration transmitting member 10 and the grasping member 56*b* of the jaw unit 5G, the contact portion 13 between the treating section 17*f* and the grasping member 56*b* provides large grasping force, and the non-contact portion 16 therebetween provides small grasping force. In this state, ultrasonic waves are supplied to the aforementioned vibration transmitting member 10.

As a result, frictional heat generated due to the ultrasonic waves is applied to the living body tissue grasped between the treating section 17*f* and the grasping member 56*b*, thereby effecting coagulation and incision of the living body tissue.

With the present embodiment, the non-contact portion 16 provides small grasping force in the same way as with the first embodiment. This reduces ultrasonic wave transmission performance, thereby producing reduced frictional heat. Accordingly, the living body tissue grasped by the non-contact portion 16 does not reach the temperature which results in incision of the living body tissue. Thus, the living body tissue is coagulated.

With such an arrangement, the stepped portions 56*b*1 and 17*f*1 are provided to the non-contact portion 16, and accordingly, the living body tissue is grasped and coagulated in a state of being tilted by virtue of the fact that the stepped portion has a difference in level.

At the same time as the coagulation of the living body tissue by the aforementioned non-contact portions 16, the contact portion 13 produces ample frictional heat due to its high ultrasonic vibration transmission performance. Accordingly, the living body tissue grasped by the contact portion 13 is coagulated and incised.

With such an arrangement, the stepped portions 56*b*1 and 17*f*1 are provided to the contact portion 13, and accordingly, the living body tissue is grasped and incised in a state of being tilted.

Thus, the present embodiment, which has a configuration in which the stepped portions 56*b*1 and the 17*f*1 are provided to the treating section 17*f* and the grasping member 56*b* so as to provide the contact portion 13 and the non-contact portions 16, provides the same advantages as those of the first embodiment.

Fourth Embodiment

Figure 19:
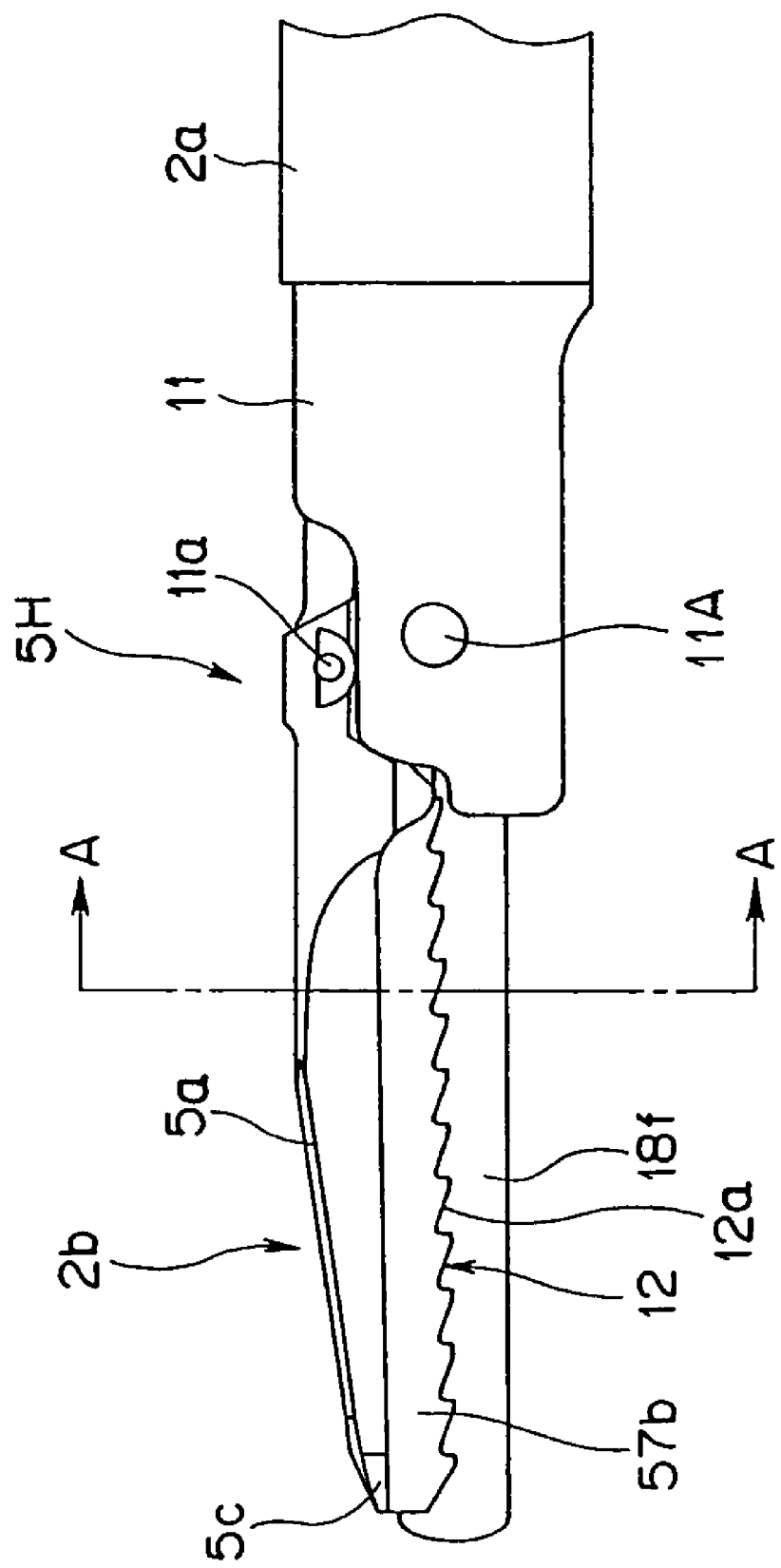
FIG. 19 is a side view which shows the configuration of a tip end treating section when the jaw unit is in a closed state, according to a fourth embodiment.
Figure 20:
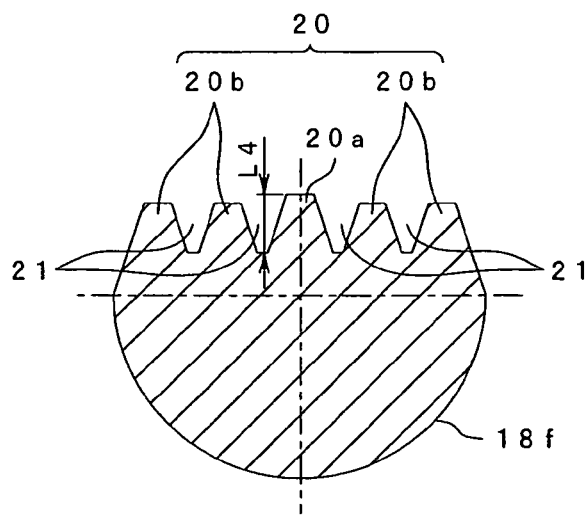
FIG. 20 is a cross-sectional view which shows the configuration of the treating section of the vibration transmitting member.
Figure 21:
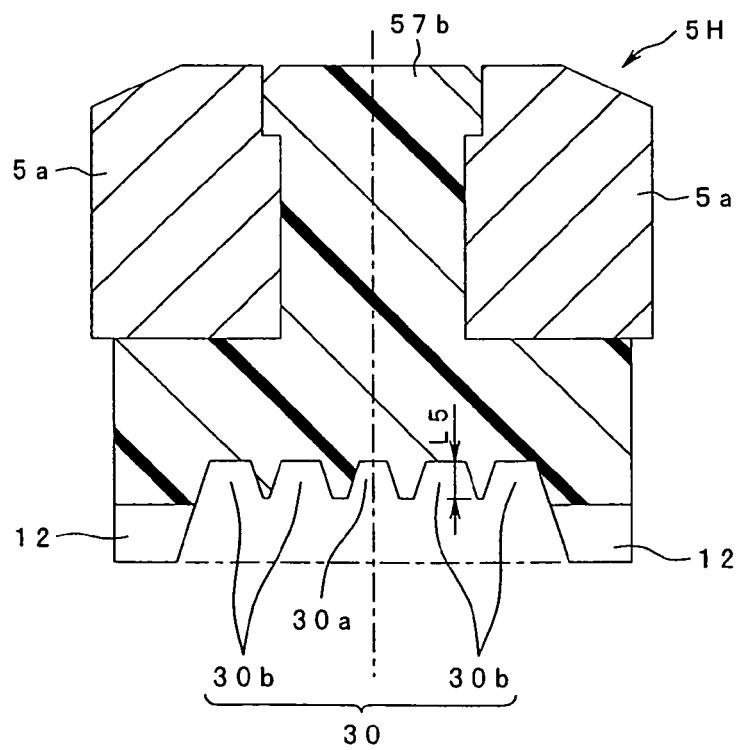
FIG. 21 is a cross-sectional view which shows the configuration of the jaw unit.
Figure 22:
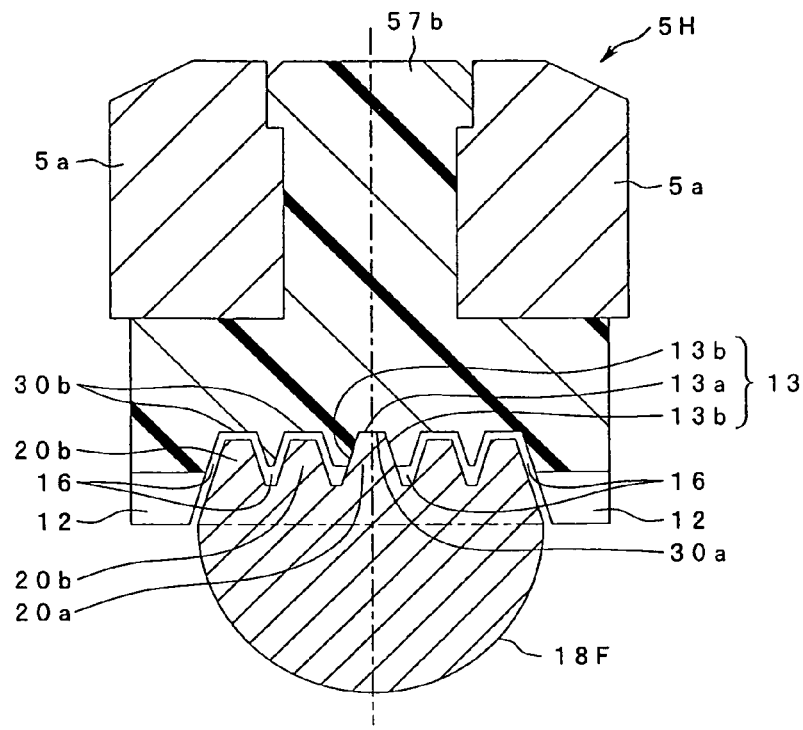
FIG. 22 is a cross-sectional view along line A-A in FIG. 19.

Next, description will be made regarding an ultrasonic coagulating cutter according to a fourth embodiment of the present invention with reference to FIG. 19 through FIG. 22. FIG. 19 is a side view which shows the configuration of a tip end treating section when the jaw unit is in a closed state, according to the fourth embodiment. FIG. 20 is a cross-sectional view which shows the configuration of the treating section of the vibration transmitting member. FIG. 21 is a cross-sectional view which shows the configuration of the jaw unit. FIG. 22 is a cross-sectional view along line A-A in FIG. 19.

In the ultrasonic coagulating cutter 1 according to the present embodiment, the contact portion 13 is formed in a staggered shape in approximately the same way as with the first embodiment. On the other hand, the non-contact portion 16 is formed in a shape which provides a large contact area for grasping living body tissue.

Specifically, as shown in FIG. 19, the ultrasonic coagulating cutter 1 according to the present embodiment includes a jaw unit 5H having a grasping member 57*b* and the vibration transmitting member 10 having a treating section 18*f*.

As shown in FIG. 20, the treating section 18*f* has an inner face (grasping face) on the side facing the aforementioned grasping member 57*b*, which is formed in a staggered structure having multiple upper faces and lower faces.

That is to say, the treating section 18*f* is formed of: a protrusion group 20 having a first protrusion 20*a* which is formed with a height L4 on the center line of the cross-section thereof, and a predetermined number of second protrusions 20*b* (four, for example) formed with a height smaller than the aforementioned height L4; and multiple recesses 21 each of which is positioned between the adjacent protrusions 20*a* or 20*b*.

That is to say, the first protrusion 20*a* of the aforementioned protrusion group 20 is for providing the contact portion 13. On the other hand, the components other than the first protrusion 20*a*, i.e., the predetermined number of second protrusions 20*b* (four, for example) and the multiple recesses 21 are for providing the non-contact portion 16.

On the other hand, the grasping member 57*b* of the jaw unit 5H has a recess group 30 which can be fit to the protrusion group 20 of the aforementioned treating section 18*f* as shown in FIG. 21.

The recess group 30 has: a first recess 30*a* which can be fit to the first protrusion 20*a* of the aforementioned treating section 18*f* such that the treating section 18*f* and the grasping member 57*b* are in surface contact with each other, thereby providing the contact portion 13; and a predetermined number of second recesses 30*b* (four, for example) each of which can be fit to the corresponding protrusion of the second protrusions 20*b* of the aforementioned treating section 18*f*, thereby providing the non-contact portion 16.

Note that the aforementioned recess group 30 is configured such that the first recess 30a and the four second recesses 30b are formed with the same depth L5.

Note that, with the present embodiment, the aforementioned protrusion group 30 and recess group 20 are formed so as to satisfy the relation L5<L4.

Upon the jaw unit 5H, which has the grasping member 57b relative to the treating section 18 having such a configuration, being turned such that it comes in a fully closed state, the jaw unit 5F has a cross-section as shown in FIG. 22.

That is to say, as shown in FIG. 22, the aforementioned contact portion 13 provides the contact face 13a approximately perpendicular to the center line of the cross-section, and the two contact faces 13b which are side faces provided to both sides of the contact face 13a, in approximately the same way as with the first embodiment. Such an arrangement provides large grasping force suitable for incising the living body tissue.

On the other hand, upon fitting the protrusion group 20 of the treating section 18f to the recess group 30 of the grasping member 57b, the non-contact portion 16 provides a gap with a predetermined size due to the difference in size between the second protrusion 20b and the second recess 30b. The size of the gap differs in a staggered manner from both sides of the contact portion 13 along a plane across which these protrusions and recesses face each other.

That is to say, the gap formed on the side of each of the recesses 21 of the treating section 18f has a greater size than that of the gap formed on the side of the second recesses 30b of the recess group 30 of the grasping member 57b and that of the gap formed on a part of the outer face thereof.

Furthermore, the non-contact portion 16 thus configured has the gap portion with an increased area. This provides an increased contact area for grasping the living body tissue. Thus, the non-contact portion 16 exhibits the increased coagulation performance due to the increased contact area while providing the small grasping force, which is suitable for coagulating the living body tissue.

Description has been made in the present embodiment regarding an arrangement in which the grasping faces of the treating section 18f and the grasping member 57b are formed in a staggered structure having multiple upper faces and lower faces (protrusion group 20, recesses 21, and recess group 30), thereby providing the contact portion 13 and the non-contact portion 16. However, the present invention is not restricted to such an arrangement. Also, an arrangement may be made in which the grasping faces of the treating section 18f and the grasping member 57b are formed in an undulating shape so as to provide the contact portion 13 and the non-contact portion 16 which has a gap.

Note that the size of the gap of the aforementioned non-contact portion 16 may be adjusted as desired so as to provide the desired grasping force for grasping the living body tissue. Note that this size L1 needs to be determined within the range of the gap sizes which enables the grasped living body tissue to be coagulated.

The other components are the same as those of the first embodiment.

Next, description will be made regarding the operations of the ultrasonic coagulating cutter 1 according to the fourth embodiment with reference to FIG. 19 and FIG. 22.

Now, let us say that a surgeon performs treatment such as coagulation and incision of living body tissue using the ultrasonic coagulating cutter 1 having such functions.

The surgeon grips so as to close the turnable handle 7 (closing operation) in the same way as in the first embodiment, whereby the jaw unit 5H is turned to a fully closed state, as to the treating section 18f of the vibration transmitting member 10, which is at a stationary position, as shown in FIG. 19. As a result, the living body tissue is grasped between the treating section 18f which is an ultrasonic probe of the vibration transmitting member 10 and the grasping member 57b of the jaw unit 5H.

In this case, with regard to the grasping force applied to the living body tissue grasped between the treating section 18f of the vibration transmitting member 10 and the grasping member 57b of the jaw unit 5H, the contact portion 13 between the treating section 18f and the grasping member 57b provides large grasping force, and the non-contact portion 16 provides small grasping force. In this state, ultrasonic waves are supplied to the aforementioned vibration transmitting member 10.

As a result, frictional heat generated due to the ultrasonic waves is applied to the living body tissue grasped between the treating section 18f and the grasping member 57b, thereby effecting coagulation and incision of the living body tissue.

With the present embodiment, the non-contact portion 16 provides small grasping force in the same way as with the first embodiment. This reduces ultrasonic wave transmission performance, thereby producing reduced frictional heat. Accordingly, the living body tissue grasped by the non-contact portion 16 does not reach the temperature which results in incision of the living body tissue. Thus, the living body tissue is coagulated.

In this case, in the non-contact portion 16 according to the present embodiment, the size of the gap portion of the non-contact portion 16 differs in a staggered manner according to the distance from the longitudinal axis of the treating section 18f and the grasping member 57b. With such an arrangement, the living body tissue is coagulated while being grasped over a large contact area. Thus, such an arrangement exhibits the greater grasping performance than that of the first embodiment.

At the same time as the coagulation of the living body tissue by the aforementioned non-contact portions 16, the contact portion 13 produces ample frictional heat due to its high ultrasonic vibration transmission performance since the grasping force is large. Accordingly, the living body tissue grasped by the contact portion 13 is coagulated and incised.

Thus, the present embodiment offers increased coagulation performance by the non-contact portion 16, in addition to the same advantages as those of the first embodiment.

Note that the treating section 18f of the vibration transmitting member 10 and the grasping member 5b of the jaw unit 5 according to the present embodiment may be configured so as to provide the contact portion 13 and the non-contact portions 16 according to a first modification and a second modification as described below.

Description will be made regarding the first modification and second modification with reference to FIG. 23 and FIG. 24. Note that FIG. 23 and FIG. 24 are cross-sectional views along line A-A in FIG. 19.

(First Modification)

Figure 23:
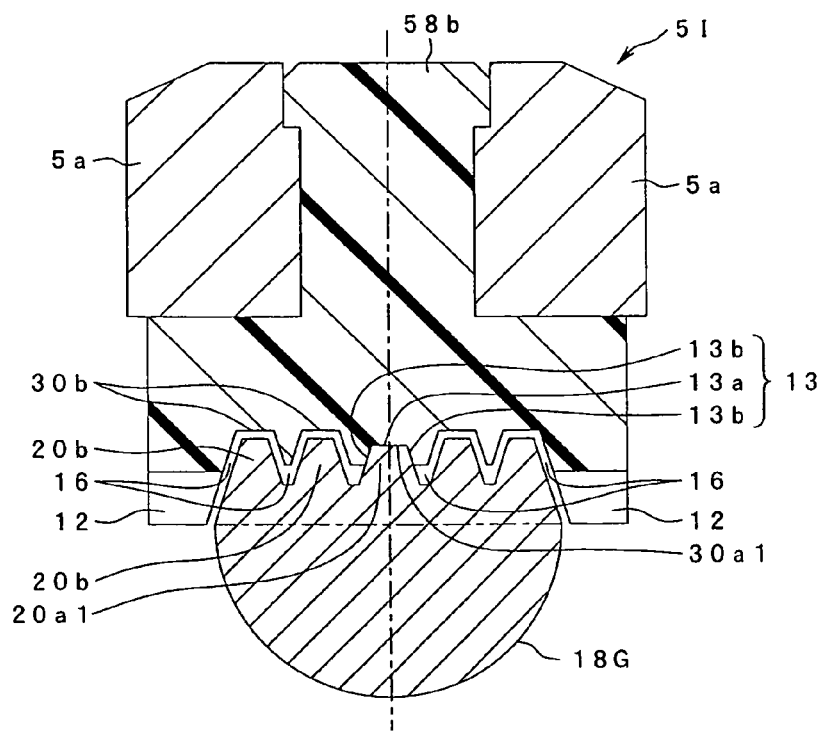
FIG. 23 is a cross-sectional view which shows the configuration of a tip end treating section according to a first modification of the fourth embodiment.
Figure 24:
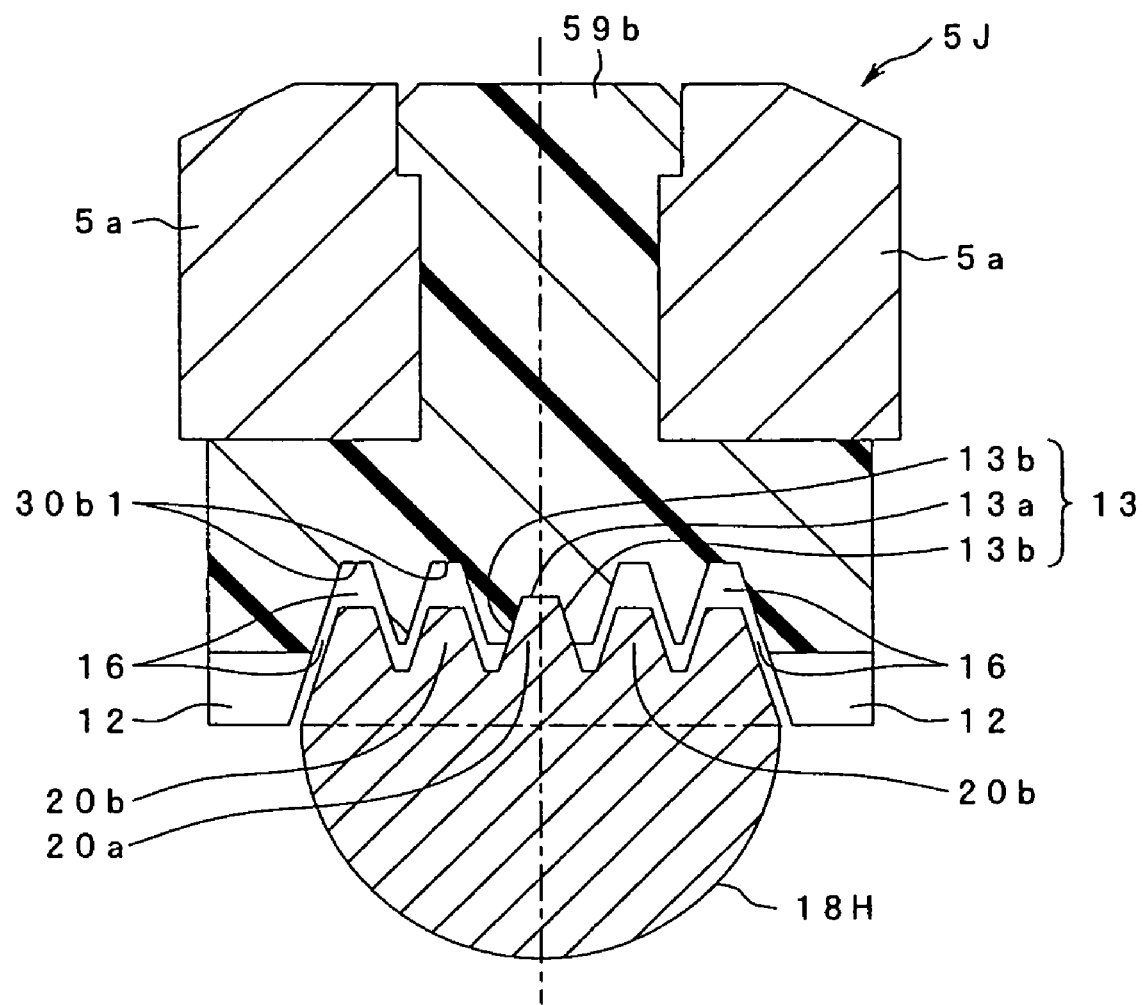
FIG. 24 is a cross-sectional view which shows the configuration of a tip end treating section according to a second modification of the fourth embodiment.

FIG. 23 is a cross-sectional view which shows the configuration of a tip end treating section according to the first modification of the fourth embodiment.

As shown in FIG. 23, the first modification is configured such that a first protrusion 20a1 of a treating section 18G and a first recess 20a1 of the grasping member 57b, which provide the contact portion 13, are formed with a height and depth smaller than those of the other protrusions and recesses, i.e., second protrusions 20b and second recesses 30b. Note that the "height and depth" as used here represent the length thereof in the direction of the center line of the cross-section of the treating section 18G.

That is to say, the contact area of the contact faces 13b which are the side faces of the contact portion 13 is smaller than that of the fourth embodiment.

The other components including the non-contact portion 16 are the same as those of the fourth embodiment described above.

Thus, while the contact portion 13 provides a reduced contact area, the aforementioned first modification provides the same functions and advantages as those of the fourth embodiment.

(Second Modification)

FIG. 24 is a cross-sectional view which shows the configuration of a tip end treating section according to the second modification of the fourth embodiment.

As shown in FIG. 24, with regard to the second modification, while the first protrusion 20a and the first recess 30a, which provide the contact portion 13, have the same structures as those of the fourth embodiment, second recesses 30b1 of a grasping member 18H, which provide the non-contact portion 16, are formed with a greater depth than that of the fourth embodiment, thereby providing a gap with an increased size at each of the second recesses 31b1.

The other components are the same as those of the fourth embodiment.

With the second modification, the non-contact portion 16 provides a gap with a larger size at each of the second recesses 30b1 than that of the other gaps, thereby providing reduced grasping force. That is to say, the size of the gaps at these second recesses 30b1 results in a smaller ultrasonic vibration transmission performance, thereby producing reduced frictional heat.

With such an arrangement, the non-contact portion 16 provides coagulation of living body tissue as follows. That is to say, the living body tissue positioned at the gaps other than the aforementioned second recesses 30b1 is coagulated in a sure manner. At the same time, the living body tissue positioned at the second recesses 30b1 is coagulated with lower coagulation performance than that of the other gaps. It is needless to say that the living body tissue can be incised using the contact portion 13 at the same time.

The other functions and advantages are the same as those of the fourth embodiment.

The present invention is not restricted to the above-described first embodiment through fourth embodiment and the above-described modifications thereof, rather, various modifications can be made without departing from the essence of the present invention.

In this invention, it is apparent that various modifications different in a wide range can be made on the basis of this invention without departing from the spirit and scope of the invention.

This invention is not restricted by any specific embodiment except being limited by the appended claims.

What is claimed is:

1. A coagulating cutter comprising:
a transmitting member for transmitting energy, for treating living body tissue, to the living body tissue;
an outer sheath through which the transmitting member is passed;
a grasping section supported at the tip end portion of the outer sheath so as to be capable of turning with respect to the transmitting member, which allows the living body tissue to be grasped against the transmitting member, a surface of the grasping section facing a surface of the transmitting member;
a recess located at a center position along a longitudinal direction of one of the facing surfaces of the transmitting member and the grasping section; and
a protrusion extending over a predetermined length in a longitudinal direction of the other of the facing surfaces of the transmitting member and the grasping section, the protrusion being configured to fit into the recess such that a gap of a predetermined dimension is formed between the facing surfaces of the transmitting member and the grasping section,
wherein, when the grasping section is turned toward the transmitting member into a closed state, the protrusion fits into the recess and is in a surface contact with the recess to form a contact portion for incising the living body tissue,
the facing surfaces of the transmitting member and the grasping section, which are positioned on both sides of the contact portion and which have the gap of the predetermined dimension, form a non-contact portion operable for coagulating the grasped living body tissue, and
the gap of the predetermined dimension of the non-contact portion is formed so as to be enlarged in a stepped manner with an increase in a distance from each side of the recess and the protrusion.

2. The coagulating cutter according to claim 1, wherein the non-contact portion is configured such that the size of the gap of the predetermined dimension employed to form the non-contact portion increases according to the increase in the distance from the axis in the predetermined length direction along a plane across which the transmitting member and the grasping section face each other.

3. The coagulating cutter according to claim 1, wherein the protrusion is formed in a rectangular or arc-shaped cross-section orthogonal to the axis in the predetermined length direction,
and wherein the recess is formed in a rectangular or arc-shaped cross-section corresponding to the structure of the protrusion.

* * * * *

UNITED STATES PATENT AND TRADEMARK OFFICE
CERTIFICATE OF CORRECTION

| | | |
|---|---|---|
| PATENT NO. | : 7,645,278 B2 | Page 1 of 1 |
| APPLICATION NO. | : 11/359535 | |
| DATED | : January 12, 2010 | |
| INVENTOR(S) | : Hiroshi Ichihashi et al. | |

It is certified that error appears in the above-identified patent and that said Letters Patent is hereby corrected as shown below:

Title Page, Item (73) should read, --(73) Assignee: Olympus Medical Systems Corp. (JP)--.

Signed and Sealed this

Fourteenth Day of December, 2010

David J. Kappos
*Director of the United States Patent and Trademark Office*